United States Patent
Goto et al.

(10) Patent No.: US 11,970,563 B2
(45) Date of Patent: Apr. 30, 2024

(54) HEAVY METAL- AND ODOUR-FREE NANOPARTICULATE COMPOSITIONS

(71) Applicants: Nanyang Technological University, Singapore (SG); Agency for Science, Technology and Research, Singapore (SG)

(72) Inventors: Atsushi Goto, Singapore (SG); Jit Sarkar, Singapore (SG); Longqiang Xiao, Singapore (SG); Feifei Li, Singapore (SG); Alexander M. Van Herk, Singapore (SG); Alexander William Jackson, Singapore (SG)

(73) Assignees: Nanyang Technological University, Singapore (SG); Agency for Science, Technology and Research, Singapore (SG)

( * ) Notice: Subject to any disclaimer, the term of this patent is extended or adjusted under 35 U.S.C. 154(b) by 906 days.

(21) Appl. No.: 16/969,808

(22) PCT Filed: Feb. 27, 2019

(86) PCT No.: PCT/SG2019/050108
§ 371 (c)(1),
(2) Date: Aug. 13, 2020

(87) PCT Pub. No.: WO2019/168471
PCT Pub. Date: Sep. 6, 2019

(65) Prior Publication Data
US 2021/0002408 A1 Jan. 7, 2021

(30) Foreign Application Priority Data
Feb. 27, 2018 (SG) .......................... 10201801591Y

(51) Int. Cl.
| | |
|---|---|
| *C08F 299/02* | (2006.01) |
| *C08F 4/08* | (2006.01) |
| *C08F 293/00* | (2006.01) |
| *A61K 9/51* | (2006.01) |
| *B82Y 30/00* | (2011.01) |
| *B82Y 40/00* | (2011.01) |

(52) U.S. Cl.
CPC ............ *C08F 299/024* (2013.01); *C08F 4/08* (2013.01); *C08F 293/005* (2013.01); *A61K 9/5138* (2013.01); *B82Y 30/00* (2013.01); *B82Y 40/00* (2013.01)

(58) Field of Classification Search
CPC .... C08F 299/024; C08F 4/08; C08F 293/005; B82Y 40/00
See application file for complete search history.

(56) References Cited

FOREIGN PATENT DOCUMENTS

CN         106519155 A     3/2017

OTHER PUBLICATIONS

Darabi et al., Macromolecule 2015 vol. 48, pp. 1952-1958 (Year: 2015).*
Sarkar et al., Polym. Chem., 2018 vol. 9, pp. 4900-4907 (Year: 2018).*
European Search Report in related application EP19761460.5 dated Nov. 2, 2021.
Goto, A. et al. Reversible Complexation Mediated Living Radical Polymerization (RCMP) Using Organic Catalysts; Macromolecules 2011, 44, 8709-8715.
Goto, A. et al.; Reversible Generation of a Carbon-Centered Radical from Alkyl Iodide Using Organic Salts and Their Application as Organic Catalysts in Living Radical Polymerization; J. Am. Chem. Soc. 2013, 135, 11131-11139.
Ohtsuki, A. et al.; Photocontrolled Organocatalyzed Living Radical Polymerization Feasible over a Wide Range of Wavelengths; J. Am. Chem. Soc. 2015, 137, 5610-5617.
Sarkar, J. et al.; Living Radical Polymerization with Alkali and Alkaline Earth Metal Iodides as Catalysts; Macromolecules 2016, 49 (14), 5033-5042.
Leswin, J. S. K. et al.; Particle Formation in RAFT-Mediated Emulsion Polymerization: A Calorimetric Study; Macromolecular Symposia, 2009, 275-276, 24-34.
Li, Y. et al.; Vesicle-templated pH-responsive polymeric nanocapsules; Angew. Chem. 2010, 122, 4136-4140.
Ali, S. I. et al.; Vesicle-templated pH-responsive polymeric nanocapsules; Soft Matter, 2011, 7, 5283-5390.
Warren, N. J. et al.; Polymerization-Induced Self-Assembly of Block Copolymer Nanoobjects via RAFT Aqueous Dispersion Polymerization; J. Am. Chem. Soc., 2014. 136, 10174-10185.
Couvreur, L. et al., First Nitroxide-Mediated Controlled Free-Radical Polymerization of Acrylic Acid; Macromolecules, 2003, 36, 8260?8267.
International Search Report and Written Opinion in related application PCT/SG2019/050108 dated Apr. 16, 2019.
Darabi, A. et al., One-Pot Synthesis of Poly((diethylamino)ethyl methacrylate-co-styrene)-b-poly(methyl methacrylate-co-styrene) Nanoparticles via Nitroxide-Mediated Polymerization. Macromolecules, Mar. 24, 2015, vol. 48, No. 7, pp. 1952-1958 Protonated Poly(DEAEMA-co-S) Macroalkoxyamine'; Table 1; Figure 2; Schemes 1 and 2.

(Continued)

*Primary Examiner* — Robert D Harlan
(74) *Attorney, Agent, or Firm* — Patterson + Sheridan, LLP

(57) ABSTRACT

The present invention relates to a nanoparticulate composition comprising nanoparticles formed from an amphipathic block copolymer comprising a hydrophilic block and a hydrophobic block, where the nanoparticles are provided in the form of micelles, cylindrical worm structures or vesicles and the size of the nanoparticles is from 25 to 500 nm, wherein: the composition is substantially free of heavy metals and compounds comprising sulfur. Also disclosed herein is a method of forming said nanoparticulate composition by polymerization induced self-assembly (PISA) via non-transition-metal catalysed controlled radical polymerization (NTMC-CRP).

19 Claims, 10 Drawing Sheets

(56) References Cited

OTHER PUBLICATIONS

Zhou, D. et al., A new paradigm in polymerization induced self-assembly (PISA): Exploitation of "non-living" addition-fragmentation chain transfer (AFCT) polymerization. Polymer Chemistry, Jun. 29, 2017, vol. 8, pp. 4177-4181.
Sarkar, J. et al., Synthesis of transition-metal-free and sulfur-free nanoparticles and nanocapsules via reversible complexation mediated polymerization (RCMP) and polymerization induced self-assembly (PISA). Polymer Chemistry, Sep. 11, 2018, vol. 9, pp. 4900-4907.
Chaduc et al.; Batch Emulsion Polymerization Mediated by Poly(methacrylic acid); MacroRAFT Agents: One-Pot Synthesis of Self-Stabilized Particles; Macromolecules, 2012, 45, 5881-5893.
Guo et al.; Self-Assembly of Poly(methacrylic acid)?b?poly(butyl acrylate); Amphiphilic Block Copolymers in Methanol via RAFT Polymerization; and during Film Formation for Wrinkly Surface Pattern; Macromolecules, 2014, 47, 165-174.
Upadhyaya et al.; Porous membranes from acid decorated block copolymer nano-objects via RAFT alcoholic dispersion polymerization; Polym. Chem., 2016, 7, 1899-1906.
Discher et al.; Polymer Vesicles, Science, 2002, 297, 967-973.
Heavy metals—Wikipedia [Retrieved from the Internet at: https://en.wikipedia.org/wiki/Heavy_metals}.
Chen et al.; Shape Control of Soft Nanoparticles and Their Assemblies; Chem. Mater., 2017, 29, 1918-1945.
Gaitzsch et al.; Engineering Functional Polymer Capsules toward Smart Nanoreactors; Chem. Rev., 2016, 116, 1053-1093.
Cui et al.; Emerging methods for the fabrication of polymer capsules; Adv. Colloid Interface Sci., 2014, 207, 14-31.
Matyjaszewski et al.; Macromolecular Engineering by Atom Transfer Radical Polymerization, J. Am. Chem. Soc., 2014, 136, 6513-6533.
Ouchi, et al.; 50th Anniversary Perspective: Metal-Catalyzed Living Radical Polymerization: Discovery and Perspective, Macromolecules, 2017, 50, 2603-2614.
Zhang et al.; Single Electron Transfer in Radical Ion and Radical-Mediated Organic, Materials and Polymer Synthesis; Chem. Rev., 2014, 114, 5848-5958.
Boyer et al.; Copper-Mediated Living Radical Polymerization (Atom Transfer Radical Polymerization and Copper(0) Mediated Polymerization): From Fundamentals to Bioapplications; Chem. Rev., 2016, 116, 1803-1949.
David et al.; Use of Iodocompounds in Radical Polymerization; Chem. Rev., 2006, 106, 3936-3962.
Nicolas et al.; Nitroxide-mediated polymerization; Prog. Polym. Sci., 2013, 38, 63-235.
Keddie et al.; RAFT Agent Design and Synthesis; Macromolecules, 2012, 45, 5321-5342.
Hill et al.; Expanding the Scope of RAFT Polymerization: Recent Advances and New Horizonsl Macromolecules, 2015, 48, 5459-5469.
S. Yamago, Precision Polymer Synthesis by Degenerative Transfer Controlled/Living Radical Polymerization Using Organotellurium, Organostibine, and Organobismuthine Chain-Transfer Agents Chem. Rev., 2009, 109, 5051-5068.
Satoh et al.; Stereospecific Living Radical Polymerization: Dual Control of Chain Length; and Tacticity for Precision Polymer Synthesis; Chem. Rev., 2009, 109, 5120-5156.
Goto et al.; Kinetics of living radical polymerization, Prog. Polym. Sci., 2004, 29, 329-385.
Ferguson et al.; Effective ab initio Emulsion Polymerization; under RAFT Control; Macromolecules, 2002, 35, 9243-9245.
Sprong et al.; Molecular Watchmaking: ab initio Emulsion; Polymerization by RAFT-controlled Self-assembly; Macromol. Symp., 2006, 231, 84-93.
Leswin et al.; Particle Formation in RAFT-Mediated Emulsion; Polymerization: A Calorimetric Study; Macromol. Symp., 2009, 275-276, 24-34.
Li et al.; RAFT Synthesis of Sterically Stabilized Methacrylic Nanolatexes and Vesicles by Aqueous Dispersion Polymerization; Angew. Chem., Int. Ed., 2010, 49, 4042-4046.
Sugihara et al.; Aqueous Dispersion Polymerization: A New Paradigm for in Situ Block Copolymer Self-Assembly in Concentrated Solution; J. Am. Chem. Soc., 2011, 133, 15707-15713.
Zhang et al.; Well-Defined Amphiphilic Block Copolymers and Nano-objects; Formed in Situ via RAFT-Mediated Aqueous Emulsion Polymerization ; Macromolecules, 2011, 44, 4149-4158.
Huang et al.; Direct preparation of vesicles from one-pot RAFT dispersion polymerization; Polymer, 2010, 51, 5115-5121.
Wan et al.; One-pot synthesis of nanomaterials via RAFT polymerization induced self-assembly and morphology transition; Chem. Commun., 2009, 5883-5885.
Derry et al.; Industrially-relevant polymerization-induced self-assembly formulations in non-polar solvents: RAFT dispersion polymerization of benzyl methacrylate; Polym. Chem., 2015, 6, 3054-3062.
Monteiro et al.; Polymer Nanoparticles via Living Radical Polymerization in Aqueous Dispersions: Design and Applications; Macromolecules, 2012, 45, 4939-4957.
Warren et al.; Polymerization-Induced Self-Assembly of Block Copolymer Nanoobjects; via RAFT Aqueous Dispersion Polymerization, J. Am. Chem. Soc., 2014, 136, 10174-10185.
Rieger; Guidelines for the Synthesis of Block Copolymer Particles of Various Morphologies by RAFT Dispersion Polymerization; Macromol. Rapid Commun., 2015, 36, 1458-1471.
Zetterlund et al.; Controlled/Living Radical Polymerization in Dispersed Systems: An Update Chem. Rev., 2015, 115, 9745-9800.
Derry et al.; Polymerization-induced self-assembly of block copolymer nanoparticles via RAFT non-aqueous dispersion polymerization; Prog. Polym. Sci., 2016, 52, 1-18.
Zhu et al.; Polymer vesicles: Mechanism, preparation, application, and responsive behavior; Prog. Polym. Sci., 2017, 64, 1-22.
Lowe, RAFT alcoholic dispersion polymerization with polymerization induced self-assembly Polymer, 2016, 106 (Supplement C), 161-181.
Canning et al.; A Critical Appraisal of RAFT-Mediated Polymerization-Induced Self-; Assembly; Macromolecules, 2016, 49, 1985-2001.
Charleux et al.; Polymerization-Induced Self-Assembly: From Soluble Macromolecules to Block Copolymer Nano-Objects in One Step' Macromolecules, 2012, 45, 6753-6765.
Sun et al.; Recent advances in RAFT dispersion polymerization for preparation of block copolymer aggregates; Polym. Chem., 2013, 4, 873-881.
Zhang, Ionic Liquids: Versatile Media for Preparation of Vesicles from Polymerization-Induced Self-Assembly; ACS Macro Lett., 2015, 4, 755-758.
Huo et al.; Morphology Evolution of Polymeric Assemblies Regulated with Fluoro-Containing Mesogen in Polymerization-Induced Self-Assembly; Macromolecules, 2017, 50, 8192-8201.
Sugihara et al.; One-Pot Synthesis of Biomimetic Shell Cross-Linked Micelles and Nanocages by ATRP in Alcohol/Water Mixtures; Angew. Chem., Int. Ed., 2010, 49, 3500-3503.
Wang et al.; Polymerization-Induced Self-Assembly (PISA) Using ICAR ATRP at Low Catalyst Concentration' Macromolecules, 2016, 49, 8605-8615.
Kapishon et al.; Polymerization Induced Self-Assembly of Alginate Based Amphiphilic Graft Copolymers Synthesized by Single Electron Transfer Living Radical Polymerization; Biomacromolecules, 2015, 16, 2040-2048.
Brusseau et al.; Nitroxide-Mediated Copolymerization of Methacrylic Acid and Sodium 4-Styrenesulfonate in Water Solution and One-Pot Synthesis of Amphiphilic Block Copolymer Nanoparticles; Macromolecules, 2011, 44, 5590-5598.
Qiao et al.; Nitroxide-mediated polymerization-induced self-assembly of amphiphilic block copolymers with a pH/temperature dual sensitive stabilizer block; Polym. Chem., 2017, 8, 4014-4029.
Delaittre et al.; Formation of polymer vesicles by simultaneous chain growth and self-assembly of amphiphilic block copolymers; Chem. Commun., 2009, 2887-2889.

(56) References Cited

OTHER PUBLICATIONS

Zhou et al.; A new paradigm in polymerization induced self-assembly (PISA): Exploitation of "non-living" addition-fragmentation chain transfer (AFCT): polymerization; Polym. Chem., 2017, 8, 4177-4181.

Lotierzo et al.; Toward Sulfur-Free RAFT Polymerization Induced Self-Assembly; ACS Macro Lett., 2017, 6, 1438-1443.

Boott et al.; Scalable and uniform 1D nanoparticles by synchronous polymerization, crystallization and self-assembly; Nat. Chem., 2017, 9, 785-792.

Smeets et al.; A simple one-step sonochemical route towards functional hairy polymer; Nanoparticles; Soft Matter, 2010, 6, 2392-2395.

Ohtsuki et al.; Photocontrolled Organocatalyzed Living Radical Polymerization; Feasible over a Wide Range of Wavelengths; J. Am. Chem. Soc., 2015, 137, 5610-5617.

Wang et al.; Solvent-Selective Reactions of Alkyl Iodide with Sodium Azide for; Radical Generation and Azide Substitution and Their Application to One-Pot Synthesis of Chain-End-Functionalized Polymers; J. Am. Chem. Soc., 2017, 139, 10551-10560.

Wang et al.; Biocompatible Choline Iodide Catalysts for Green Living Radical Polymerization of Functional Polymers; ACS Macro Lett., 2018, 7, 263-268.

Figg et al.; Polymerization-induced thermal self-assembly (PITSA); Chem. Sci., 2015, 6, 1230-1236.

Karagoz et al.; Polymerization-Induced Self-Assembly (PISA)—control over the morphology of nanoparticles for drug delivery applications; Polym. Chem., 2014, 5, 350-355.

\* cited by examiner

HEAVY METAL- AND ODOUR-FREE NANOPARTICULATE COMPOSITIONS

FIELD OF INVENTION

This invention relates to a nanoparticulate composition formed from an amphipathic block copolymer, which is substantially free of sulfur-containing compounds and heavy metals, and a method of making said material.

BACKGROUND

The listing or discussion of a prior-published document in this specification should not necessarily be taken as an acknowledgement that the document is part of the state of the art or is common general knowledge.

Amphiphilic block polymers with water-soluble and water-insoluble segments self-assemble in selective solvents. The self-assemblies can be spherical micelles, worm-like micelles, micellar gels, toroids, and spherical vesicles, depending on the solvents, temperatures, and volume fractions (molecular weights) of hydrophilic and hydrophobic segments. Such self-assemblies are extensively used to create advanced materials for use in drug delivery, cosmetics, and energy-related applications.

Controlled radical polymerisation (CRP) is an efficient method for synthesising well-defined amphiphilic block copolymers. The self-assemblies can be obtained from pre-synthesised block copolymers, in which the block copolymer is first dissolved in a good solvent that dissolves both the hydrophilic and hydrophobic segments. This is then followed by the addition of a non-solvent that selectively precipitates one segment of the polymer to induce self-assembly. A limitation of this method is that the self-assemblies can only be obtained in dilute conditions (since the polymer concentration is usually less than 1 wt % in the solution), but does not give stable self-assemblies at high polymer concentrations. This dilution (low productivity) limits the commercial utility of this process for the formation of vehicles for the delivery of active agents.

Polymerisation-induced self-assembly (PISA) has been developed as an efficient method to overcome this limitation. PISA affords high colloidal stability of the generated self-assemblies even at high polymer concentrations (high solid contents) (up to 25 wt %). PISA is an emerging technique which takes place in situ during a block copolymerisation to generate self-assemblies. Typically, a hydrophilic monomer A is first polymerised in a hydrophilic solvent, followed by the use of a hydrophobic monomer B for the chain extension (block polymerisation). As the polymer chain grows, it changes from soluble to surface active due to the generated hydrophobic B segment which is insoluble in the solvent. As such, self-assemblies are generated during the polymerisation process. Spherical micelles (particles), worms (cylinders), and vesicles (capsules) can be generated, depending on the solvents, temperatures, and molecular weights of the A and B segments.

Reversible addition-fragmentation chain transfer (RAFT) polymerisation is a common technique used for PISA in many cases. Water, ethanol, n-alkanes, and ionic liquids, for example, are used as solvents. Atom transfer radical polymerisation (ATRP) is also used for PISA. A drawback of RAFT polymerisation is that it uses sulfur-containing compounds, which causes undesired colouring and unpleasant odour in the products. On the other hand, ATRP uses transition metals (heavy metals), which are not biologically- and environmentally friendly. The use of an odour-free and heavy metal-free technique is highly preferred for biomedical, healthcare, cosmetics, and agrochemical release applications.

Given this, there remains a need to develop new synthesis methods that produce polymeric self-assemblies or compositions, and at the same time do not involve sulfur-containing compounds and heavy metals during the process, thereby making them more suitable for biological applications. More importantly, these methods have to be robust, cost-effective and versatile, such that self-assemblies with various morphologies can be achieved easily.

SUMMARY OF INVENTION

Aspects and embodiments of the invention are provided by the following numbered embodiments.

1. A nanoparticulate composition comprising:
   nanoparticles formed from an amphipathic block copolymer comprising a hydrophilic block and a hydrophobic block, where the nanoparticles are provided in the form of micelles, cylindrical worm structures or vesicles and the size of the nanoparticles is from 25 to 500 nm, wherein:
   the composition is substantially free of compounds comprising sulfur; and
   the composition is substantially free of a heavy metal 2. The composition according to Clause 1, wherein the amphipathic block copolymers are terminated by a halogen atom.

3. The composition according to Clause 1 or Clause 2, wherein the composition further comprises an active agent encapsulated in the nanoparticles.

4. The composition according to Clause 3, wherein the active agent is selected from one or more of the group consisting of vitamin C, peptides, glycerol, dyes, flavours, perfume oils, citronellal, silicon oils, organosilicons, pesticides, Beta-carotene and a pharmacologically active agent (e.g. ibuprofen, fenofibrate, and isotrentinoin).

5. The composition according to any one of the preceding clauses, wherein:
   the amount of compounds comprising sulfur in the composition is from 0 to 0.01 wt %; and/or
   the amount of heavy metal in the composition is from 0 to 0.01 wt %.

6. The composition according to any one of the Clauses 2 to 5, wherein the halogen atom is iodine.

7. The composition according to any one of the preceding clauses, wherein when the nanoparticles are in the form of a vesicle, the amphipathic block copolymer is arranged in the form of a membrane with an outer and inner surface, which inner surface defines a core region.

8. The composition according to Clause 7, wherein the core region comprises an active agent and/or a liquid.

9. The composition according to Clause 7 or Clause 8, wherein the amphipathic block copolymer is arranged so that the outer and inner surface of the membrane are formed from the hydrophilic blocks of the copolymer, optionally wherein the amphipathic block copolymer has an average ratio of hydrophobic repeating units to hydrophilic repeating units of from 1:9 to at least 9:1, such as from 1:1 to 5000:1, such as from 4:1 to 2000:1, such as from 9:1 to 1000:1.

10. The composition according to Clause 9, wherein the composition further comprises a hydrophilic active agent that is substantially encapsulated in the core region of the vesicle.

11. The composition according to Clause 9 or Clause 10, wherein the composition further comprises a hydrophobic active agent that is substantially encapsulated in the membrane of the vesicle.

12. The composition according to any one of Clauses 9 to 11, wherein the composition further comprises a polar liquid that is encapsulated in the core region of the vesicle, optionally wherein the polar liquid is selected from one or more of the group consisting of water, a $C_{1-6}$ monoalcohol, a $C_{3-6}$ ketone, a glycol, acetonitrile, an amide, and a sulfoxide.

13. The composition according to Clause 7 or Clause 8, wherein the amphipathic block copolymer is arranged so that the outer and inner surface of the membrane are formed from the hydrophobic blocks of the copolymer, optionally wherein the amphipathic block copolymer has an average ratio of hydrophilic repeating units to hydrophobic repeating units of from 1:9 to at least 9:1, such as from 1:1 to 5000:1, such as from 4:1 to 2000:1, such as from 9:1 to 1000:1.

14. The composition according to Clause 13, wherein the composition further comprises a hydrophobic active agent that is substantially encapsulated in the core region of the vesicle.

15. The composition according to Clause 13 or Clause 14, wherein the composition further comprises a hydrophilic active agent that is substantially encapsulated in the membrane of the vesicle.

16. The composition according to any one of Clauses 13 to 15, wherein the composition further comprises a non-polar liquid that is encapsulated in the core region of the vesicle, optionally wherein the non-polar liquid is selected from one or more of the group consisting of a $C_{5-10}$ alkane, a $C_{5-10}$ alkene, a $C_{5-10}$ alkyne, and a $C_{6-10}$ arene, where said non-polar liquids are unsubstituted or substituted by one or more halogen atoms.

17. The composition according to any one of Clauses 7 to 16, wherein the vesicle has an average diameter of from 100 to 500 nm.

18. The composition according to any one of Clauses 1 to 6, wherein when the nanoparticles are in the form of a micelle, the amphipathic block copolymer has an average ratio of hydrophobic repeating units to hydrophilic repeating units of from 1:100 to 10:1, such as from 1:10 to 10:1, such as from 1:1 to 5:1, such as from 1.8:1 to 4:1, or vice versa.

19. The composition according to Clause 18, wherein the micelle has an average diameter of from 25 to 100 nm, such as from 28 to 80 nm.

20. The composition according to any one of Clauses 1 to 6, wherein when the nanoparticles are in the form of cylindrical worm structures, the amphipathic block copolymer has an average ratio of hydrophobic repeating units to hydrophilic repeating units of from 1:1 to 100:1, such as from 4:1 to 9:1, or vice versa.

21. The composition according to Clause 20, wherein the cylindrical worm structures have an average diameter of from 50 to 200 nm, such as from 70 to 150 nm.

22. The composition according to any one of the preceding clauses, wherein the amphipathic block copolymer is a poly(acrylic acid-co-acrylate ester) or a poly(polyethylene glycol ether methacrylate)-co-acrylate ester, optionally where the amphipathic block copolymer is poly(methacrylic acid-co-methyl methacrylate) and/or poly((polyethylene glycol monomethyl ether methacrylate)-co-methyl methacrylate).

23. The composition according to any one of the preceding clauses, wherein the amphipathic block copolymer is crosslinked.

24. A method of forming a nanoparticulate composition according to any one of Clauses 1 to 22 using polymerisation induced self-assembly, the method comprising the step of forming a block copolymer by reacting a monomeric material with a macroinitiator compound in the presence of an initiator compound, a catalyst and a solvent, wherein:
    if the monomeric material polymerises to provide a hydrophobic polymer block, then the macroinitiator compound is a hydrophilic polymer or oligomer or if the monomeric material polymerises to provide a hydrophilic block, then the macroinitiator compound is a hydrophobic polymer or oligomer;
    the macroinitiator compound is terminated with a halogen atom;
    the monomeric material, the macroinitiator compound, the initiator compound, the catalyst and the solvent are all substantially free of compounds comprising sulfur; and
    the monomeric material, the macroinitiator compound, the initiator compound, the catalyst and the solvent are all substantially free of a heavy metal.

25. The method according to Clause 24, wherein the catalyst is a metal halide, where the halogen atom and halide atom have the same atomic number, and where the metal is selected from sodium, potassium, magnesium, and calcium.

26. The method according to Clause 25, wherein the metal halide is sodium iodide.

27. The method according to any one of Clauses 24 to 26, wherein the halogen atom in the macroinitiator compound is iodine.

28. The method according to any one of Clauses 24 to 27, wherein the initiator compound is an azo initiator, optionally wherein the azo initiator is 2,2'-azobis(2,4-dimethylvaleronitrile).

29. The method according to any one of Clauses 24 to 28, wherein the macroinitiator compound contains an average of from 1 to 1000 repeating units, such as from 5 to 100 repeating units, such as from 10 to 20 repeating units.

30. The method according to any one of Clauses 24 to 29, wherein the monomeric material is an acrylate ester (e.g. methyl methacrylate), and the macroinitiator compound is a poly(acrylic acid) or an oligo(acrylic acid) (e.g. poly(methylacrylic acid) or an oligo(methacrylic acid)).

31. The method according to Clause 30, wherein the solvent is a polar solvent, optionally wherein the solvent is selected from one or more of the group consisting of water, a $C_{1-6}$ monoalcohol, a $C_{3-6}$ ketone, a glycol, acetonitrile, an amide, and a sulfoxide.

32. The method according to Clause 30 or Clause 31, wherein the macroinitiator compound has the formula I:

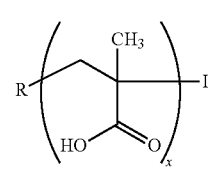

I where x is from 1 to 1000, such as from 5 to 100, such as from 10 to 20; and

R is a branched or unbranched $C_{1-10}$ alkyl group that is unsubstituted or substituted by one or more of CN, aryl and $CO_2R'$, where R' is H or a $C_{1-6}$ alkyl group, optionally wherein R is —$CH(CH_3)_2CN$.

33. The method according to any one of Clauses 24 to 29, wherein the monomeric material is an acrylic acid (e.g. methacrylic acid) and the macroinitiator compound is a poly(acrylate ester) or an oligo(acrylate ester), such as poly(methacrylate) or oligo(methacrylate).

34. The method according to Clause 33, wherein the solvent is a non-polar solvent, optionally wherein the solvent is selected from one or more of the group consisting of a $C_{5-1}$a alkane, a $C_{5-10}$ alkene, a $C_{5-10}$ alkyne, and a $C_{6-10}$ arene, where said non-polar liquids are unsubstituted or substituted by one or more halogen atoms.

35. The method according to Clause 33 or Clause 34, wherein the macroinitiator compound has the formula II:

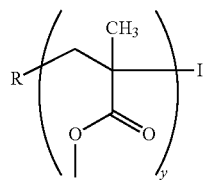

where y is from 1 to 1000, such as from 5 to 100, such as from 10 to 20; and

R is a branched or unbranched $C_{1-10}$ alkyl group that is unsubstituted or substituted by one or more of CN, aryl and $CO_2R'$, wherein R' is H or a $C_{1-6}$ alkyl group, optionally wherein R is —$CH(CH_3)_2CN$.

36. The method according to any one of Clauses 24 to 35, wherein:
(a) the molar ratio of monomeric material to macroinitiator compound in the solvent is from 30:1 to 500:1, such as from 50:1 to 300:1; and/or
(b) the molar ratio of monomeric material to catalyst in the solvent is from 150:1 to 300:1, such as from 190:1 to 200:1; and/or
(c) the molar ratio of monomeric material to initiator in the solvent is from 150:1 to 300:1, such as from 190:1 to 200:1.

37. The method according to any one of Clauses 24 to 36, wherein the step of forming a block copolymer is conducted in the presence of a crosslinking agent, optionally wherein the crosslinking agent is an ethylene glycol diacrylate ester (e.g. ethylene glycol dimethyacrylate) when the monomeric material is an acrylate ester or is an ethylene glycol diacrylic acid (e.g. ethylene glycol dimethacrylic acid) when the monomeric material is an acrylic acid.

38. The method according to Clause 37, wherein the molar ratio of monomeric material to crosslinking agent in the solvent is from 10:1 to 50:1, such as from 20:1 to 40:1.

39. The method according to any one of Clauses 24 to 38, wherein the step of forming a block copolymer is conducted in the presence of an active agent.

40. The method according to Clause 39, wherein the molar ratio of monomeric material to active agent in the solvent is from 1:1 to 300:1. Such as from 100:1 to 250:1. Such as from 150:1 to 225:1, such as from 190:1 to 200:1.

41. The method according to any one of Clauses 24 to 38, wherein after the nanoparticle has been formed an active agent is encapsulated into the nanoparticle by osmosis.

42. The method according to any one of Clauses 39 to 41, wherein the active agent is selected from one or more of the group consisting of vitamin C, peptides, glycerol, dyes, flavours, perfume oils, citronellal, silicon oils, organosilicons, pesticides, Beta-carotene and a pharmacologically active agent (e.g. ibuprofen, fenofibrate, and isotrentinoin).

43. The method according to any one of Clauses 24 to 42, wherein the nanoparticles are obtained as vesicles when the molar ratio of monomeric material to macroinitiator compound in the solvent is from 100:1 to 500:1, such as from 110:1 to 300:1 and the reaction is allowed to occur for a period of time such that an average ratio of monomeric material repeating units to macroinitiator repeating units from 1:9 to at least 9:1, such as from 1:1 to 5000:1, such as from 4:1 to 2000:1, such as from 9:1 to 1000:1 is obtained.

44. The method according to any one of Clauses 24 to 42, wherein the nanoparticles are obtained as micelles when the molar ratio of monomeric material to macroinitiator compound in the solvent is from 40:1 to 100:1, such as from 60:1 to 90:1 and the reaction is allowed to occur for a period of time such that an average ratio of monomeric material repeating units to macroinitiator repeating units from 1:100 to 10:1, such as from 1:10 to 10:1, such as from 1:1 to 5:1, such as from 1.8:1 to 4:1 is obtained.

45. The method according to any one of Clauses 24 to 42, wherein the nanoparticles are obtained as cylindrical worm structures when the molar ratio of monomeric material to macroinitiator compound in the solvent is from 40:1 to 200:1, such as from 60:1 to 150:1 and the reaction is allowed to occur for a period of time such that an average ratio of monomeric material repeating units to macroinitiator repeating units from 1:1 to 100:1, such as from 4:1 to 9:1 is obtained.

46. The method according to any one of Clauses 24 to 45, wherein the macroinitiator compound is formed by polymerising a monomeric material with a dormant initiator compound in the presence of an initiator compound, a catalyst and a solvent, wherein
the dormant initiator compound is a hydrocarbon comprising a halogen atom;
the monomeric material, the dormant initiator compound, the initiator compound, the catalyst and the solvent are all substantially free of compounds comprising sulfur; and
the monomeric material, the dormant initiator compound, the initiator compound, the catalyst and the solvent are all substantially free of a heavy metal.

47. The method according to Clause 46, wherein the catalyst is a metal halide, where the halogen atom and halide atom have the same atomic number, and where the metal is selected from sodium, potassium, magnesium, and calcium.

48. The method according to Clause 47, wherein the metal halide is sodium iodide.

49. The method according to any one of Clauses 46 to 48, wherein the halogen atom in the dormant initiator compound is iodine.

50. The method according to any one of Clauses 46 to 49, wherein the initiator compound is an azo initiator, optionally wherein the azo initiator is 2,2'-azobis(2,4-dimethylvaleronitrile).

51. The method according to any one of Clauses 46 to 50, wherein the macroinitiator compound contains an average of from 1 to 1000 repeating units, such as from 5 to 100 repeating units, such as from 10 to 20 repeating units.

52. The method according to any one of Clauses 46 to 51, wherein the dormant initiator compound 2-iodo-2-methylpropionitrile.

DRAWINGS

FIG. 1 Depicts: (a) the reversible activation of non-transition-metal catalysed controlled radical polymerisation (NTMC-CRP); and (b) the synthesis of PMAA-I and PMAA$_x$-PMMA$_y$ (an embodiment of the current invention) by NTMC-CRP and PISA (via NTMC-CRP), respectively.

FIG. 2 Depicts the synthesis and characterisation of PMAA$_{20}$-PMMA$_{180}$ in MMA/PMAA-I/NaI/V65/ethanol system (60° C.), where [MMA]o=8 M, [PMAA-I]$_0$=27 mM, [NaI]$_0$=40 mM, [V65]$_0$=40 mM, ethanol=90 wt % (Table 2, entry 11): (a) GPC chromatograms showing the elution time at 0 h and 14 h; (b) a plot of In([M]$_0$/[M]) vs. time; (c) plots of M$_n$ and M$_w$/M$_n$ vs. monomer conversion; and TEM images of the respective samples generated at 14 h: (di-ii) the dried sample of the aqueous treated solution (i shows the initial characterisation, while ii shows the subsequent characterisation); (e) dried sample of the ethanol reaction solution; and (f) cryo-TEM images of the aqueous treated solution. Note: (dii) is the same TEM image as that of FIG. 3(N).

FIG. 3 Depicts a phase diagram of the self-assemblies (A-N) generated in the PISA process for PMAA$_x$-PMMA$_y$ under various conditions as listed in Table 2. The solid content was 5-9 wt % (except the soluble phase). W+V denotes a mixture of worms and vesicles. The labels (A-N) correspond to the respective TEM images in FIG. 4.

FIG. 4. Depicts the TEM images of the self-assemblies generated in the PISA process in ethanol, according to the various conditions listed in Table 2: (A) PMAA$_5$-PMMA$_{22}$; (B) PMAA$_5$-PMMA$_{40}$; (C) PMAA$_5$-PMMA$_{86}$; (D) PMAA$_5$-PMMA$_{177}$; (E) PMAA$_{11}$-PMMA$_{42}$; (F) PMAA$_{11}$-PMMA$_{65}$; (G) PMAA$_{11}$-PMMA$_{95}$; (H) PMAA$_{11}$-PMMA$_{186}$; (I) PMAA$_{20}$-PMMA$_{60}$; (K) PMAA$_{20}$-PMMA$_{95}$; (L) PMAA$_{20}$-PMMA$_{150}$; and (N) PMAA$_2$-PMMA$_{180}$.

FIG. 5 Depict the DLS curves before (dashed lines) and after (solid lines) the addition of an aqueous NaOH solution to: (a) PMAA$_{20}$-PMMA$_{60}$; (b) PMAA$_{20}$-PMMA$_{85}$; and (c) PMAA$_{20}$-PMMA$_{160}$ (Table 2, entries 8-10). The corresponding TEM images of PMAA$_{20}$-PMMA$_{60}$, PMAA$_{20}$-PMMA$_{85}$, and PMAA$_{20}$-PMMA$_{160}$, before the addition of NaOH solution, are as shown in (I), (J) and (M), respectively.

FIG. 6 Depicts the DLS curves before (dashed lines) and after (solid lines) the addition of NaOH to: (a) PMAA$_{20}$-(PMMA/PEGDMA)$_{60}$; (b) PMAA$_{20}$-(PMMA/PEGDMA)$_{85}$; and (c) PMAA$_{20}$-(PMMA/PEGDMA)$_{160}$ (Table 3). The corresponding TEM images of PMAA$_{20}$-(PMMA/PEGDMA)$_{60}$, PMAA$_{20}$-(PMMA/PEGDMA)$_{85}$, and PMAA$_{20}$-(PMMA/PEGDMA)$_{160}$, before and after the addition of NaOH solution, are as shown in (O and R), (P and S) and (Q and T), respectively.

Figure 17:
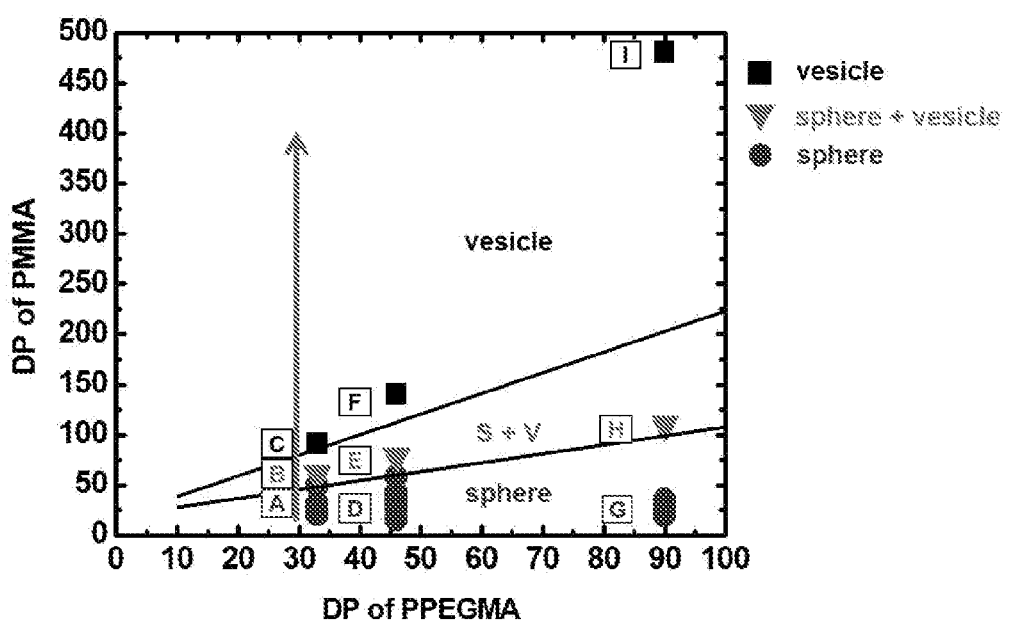

FIG. 17 Depicts the phase diagram of the self-assemblies generated in the aqueous emulsion PISA process of PPEGMA$_x$-PMMA$_y$. The solid content was 4-9 wt %. S+V denotes a mixture of spheres and vesicles.

Figure 18:
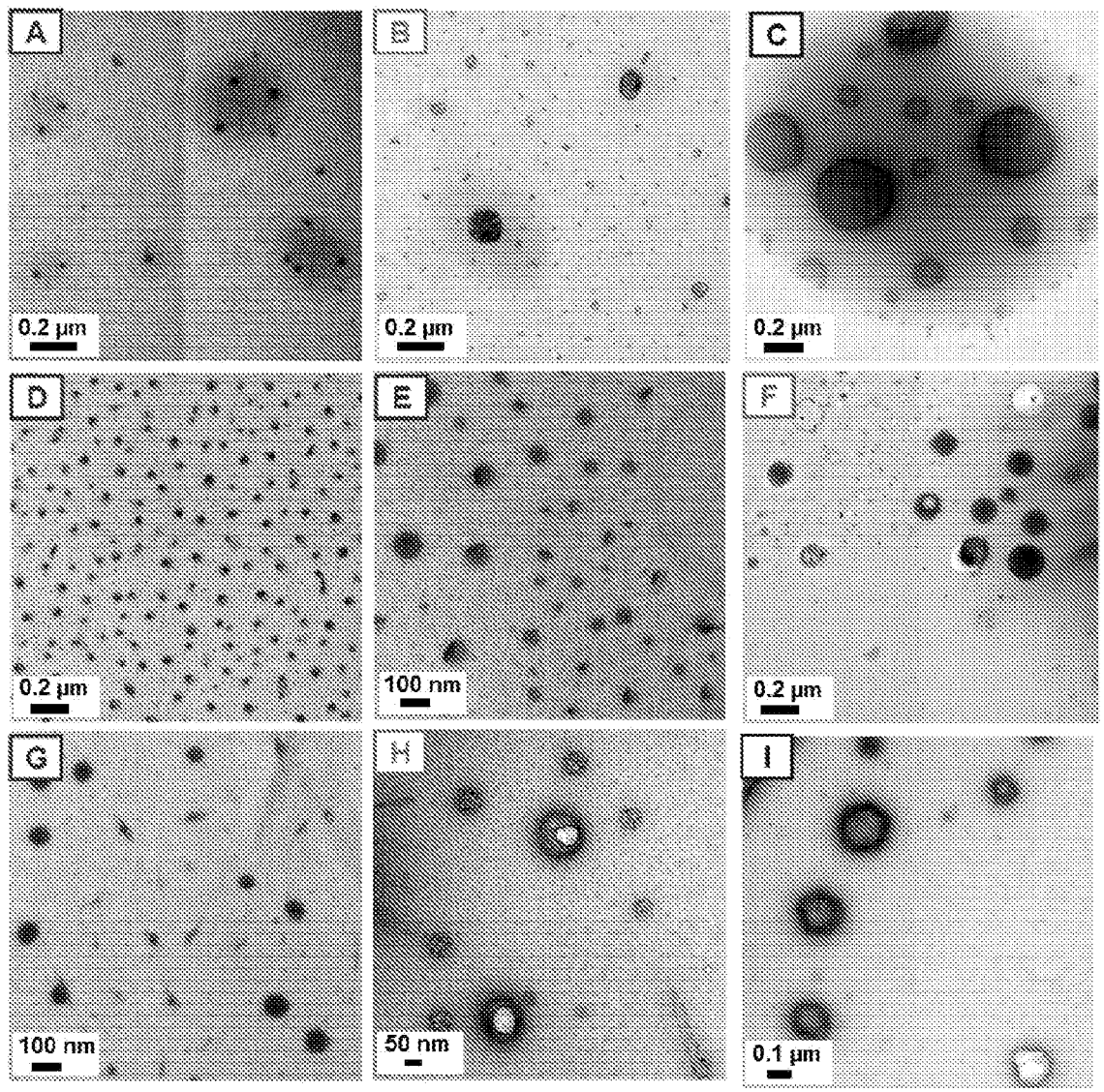

FIG. 18 Depicts the TEM images of the self-assemblies obtained in the aqueous emulsion PISA process: (A) PPEGMA$_{33}$-PMMA$_{31}$; (B) PPEGMA$_{33}$-PMMA$_{61}$; (C) PPEGMA$_{33}$-PMMA$_{91}$; (D) PPEGMA$_{46}$-PMMA$_{26}$; (E) PPEGMA$_{46}$-PMMA$_{78}$; (F) PPEGMA$_{46}$-PMMA$_{140}$; (G) PPEGMA$_{90}$-PMMA$_{25}$; (H) PPEGMA$_{90}$-PMMA$_{110}$; and (I) PPEGMA$_{90}$-PMMA$_{480}$.

DESCRIPTION

Thus, in a first aspect of the invention, there is provided a nanoparticulate composition comprising:
nanoparticles formed from an amphipathic block copolymer comprising a hydrophilic block and a hydrophobic block, where the nanoparticles are provided in the form of micelles, cylindrical worm structures or vesicles and the size of the nanoparticles is from 25 to 500 nm, wherein:
the composition is substantially free of compounds comprising sulfur; and
the composition is substantially free of a heavy metal.

In embodiments herein, the word "comprising" may be interpreted as requiring the features mentioned, but not limiting the presence of other features. Alternatively, the word "comprising" may also relate to the situation where only the components/features listed are intended to be present (e.g. the word "comprising" may be replaced by the phrases "consists of" or "consists essentially of"). It is explicitly contemplated that both the broader and narrower interpretations can be applied to all aspects and embodiments of the present invention. In other words, the word "comprising" and synonyms thereof may be replaced by the phrase "consisting of" or the phrase "consists essentially of" or synonyms thereof and vice versa.

When used herein, the term "micelle" refers to a spheroidal nanoparticle that is a two-layer structure formed from a solid core and a solid shell (i.e. sphere is not hollow). In other words, the core and shell are formed from the polymeric material, with the hydrophilic blocks on the exterior surface of the nanoparticle (to form the shell) and the hydrophobic blocks forming the core of the nanoparticle (or vice versa). While the shell is solid, these nanoparticles can still be used as a carrier because other molecules (e.g. active agents) can still be dispersed within the core of the micelle (e.g. by diffusion or other suitable means), thereby allowing the micelle to act as a carrier for an active agent.

When used herein, the term "cylindrical worm structure" refers to a solid nanoparticulate material that is similar to a micelle in that it has a solid core and a solid shell (i.e. the interior portion of the cylinder is not hollow). In other words, the core and shell are formed from the polymeric material, with the hydrophilic blocks on the exterior surface of the nanoparticle (to form the shell) and the hydrophobic blocks forming the core of the nanoparticle (or vice versa). While the shell is solid, these nanoparticles can still be used as a carrier because other molecules (e.g. active agents) can still be dispersed within the core of the cylindrical worm structure (e.g. by diffusion or other suitable means), thereby allowing the cylindrical worm structure to act as a carrier for an active agent.

When used herein, the term "vesicle" refers to a spheroidal nanoparticle structure that has a hollow core and a solid shell. The solid shell is formed by a bilayer of the amphipathic block copolymer, with outer and inner surfaces of the shell being formed by the hydrophilic blocks and the hydrophobic blocks therebetween (or vice versa).

As noted above, one of the problems encountered with prior methods of constructing nanoparticles of the kind described herein is that the process used to manufacture them makes use of a heavy metal and so the final products are commonly contaminated with said heavy metals, which are hard (if not impossible) to remove from the final compositions without removing the desired active agents and/or destroying the assembled nanoparticles. When used herein the term "heavy metal" may refer to a metal having a density greater than 5 g/cm$^3$. For example, the heavy metal may be any of titanium, vanadium, chromium, manganese, iron, cobalt, nickel, copper, zinc, gallium, germanium, arsenic, zirconium, niobium, molybdenum, technetium, ruthenium, rhodium, palladium, silver, cadmium, indium, tin, tellurium, lutetium, hafnium, tantalum, tungsten, rhenium, osmium, iridium, platinum, gold, mercury, thallium, lead, bismuth, polonium, astatine, lanthanum, cerium, praseodymium, neodymium, promethium, samarium, europium, gadolinium, terbium, dysprosium, holmium, erbium, thulium, ytterbium, actinium, thorium, protactinium, uranium, neptunium, plutonium, americium, curium, berkelium, californium, einsteinium, fermium, nobelium, radium, lawrencium, rutherfordium, dubnium, seaborgium, bohrium, hassium, meitnerium, darmstadtium, roentgenium, copernicium, and elements 113-118. Particular heavy metals that may be important to ensure are not present (or are only present in minute quantities) in the composition include radioactive elements and toxic heavy metals such as cadmium, mercury, lead, chromium and arsenic.

As noted above, the nanoparticulate composition is substantially free of heavy metals, such as those referred to above. In this context, "substantially free" may refer to the situation where there is absolutely no heavy metal present, or it may refer to a situation where the level of heavy metal is below the limits of detection of the analytical equipment used to conduct the analysis, or it may refer to a situation where only a very small amount of heavy metal is present. For example, in embodiments of the current invention, the amount of heavy metal in the composition may be from 0 to 0.01 wt %, such as from 0 to 0.0001 wt %.

As will be appreciated, the reduction or elimination of heavy metals from the nanoparticulate compositions disclosed herein (due to the processes of manufacture detailed below) makes these products more suitable for use in a biological system, such as a human or animal patient and for use in medical, healthcare, cosmetics, and agrochemical release applications. This is because the nanoparticulate compositions disclosed herein will be significantly less toxic to such subject due to the substantial reduction or entire elimination of heavy metals from the composition.

For similar reasons to the presence of heavy metals, the previous methods used to make such nanoparticulate compositions often used compounds that comprise sulfur. While the presence of such compounds may not be toxic, they tend to have an unpleasant odour, which may be off-putting. As such, the nanoparticles and nanoparticulate compositions disclosed herein may be substantially free of compounds that comprise sulfur. More particularly, the compounds that contain sulfur may be compounds that comprise sulfur in a form that causes an odour, such as a thiol, thiocarboxylic acid, thioesters, thiocarbonates, and thiocarbamates. In this context, "substantially free" may refer to the situation where there is absolutely no compounds that comprise sulfur present, or it may refer to a situation where the level of the sulfur comprising compound is below the limits of detection of the analytical equipment used to conduct the analysis, or it may refer to a situation where only a very small amount of a compound that comprises sulfur is present. For example, in embodiments of the current invention, the amount of a compound that comprises sulfur in the composition may be from 0 to 0.01 wt %, such as from 0 to 0.0001 wt %. For the avoidance of doubt, when used herein "a compound that comprises sulfur" refers to compounds produced as a by-product, as an impurity or in some other incidental manner in the manufacture of the nanoparticulate composition. This term is not intended to exclude the inclusion of active agents that comprise sulfur, which agents would be introduced intentionally into the composition and which may contain a sulfur atom (or atoms) in a form that does not produce a disagreeable odour.

As will be appreciated, the reduction or elimination of unpleasant odours from a composition makes it significantly easier to provide to a human or animal subject, or to use such compositions in other settings such as healthcare, cosmetics, and agrochemical release applications. This is because it reduces the need to include further ingredients in the composition to mask the unpleasant odour/taste associated with compounds that contain sulfur, which may increase patient compliance for pharmaceutical preparations making use of such compositions and increase customer compliance for medical, healthcare, cosmetics, and agrochemical release applications.

In particular embodiments that may be mentioned herein, the amphipathic block copolymers may be terminated by a halogen atom. The presence of the halogen atom is the result of the method of manufacture of the compositions disclosed herein. However, it is possible to remove the halogen atom and replace it by, for example, hydrogen, lactones, hydroxyl, thiol, carboxylic acid, amines, different halogen and so on, using sodium borohydride, sodium hydroxide, sodium carbonate, tributylamine, amino ethanol, cysteine, amino ethyl carboxylic acid, diaminoethane, sodium chloride, sodium bromide, sodium iodide and so on, for example. When used herein, the term "halogen atom" refers to an atom of iodine, chlorine and bromine In yet further embodiments of the invention that may be mentioned herein, when present, the halogen atom that terminates the amphipathic block copolymers may be iodine.

As will be noted from the above disclosure, the nanoparticulate compositions disclosed herein may be used as a vehicle for an active agent. In other words, said nanoparticulate compositions may further comprise an active agent encapsulated in the nanoparticles. When used herein, the term "encapsulated" refers to the enclosure of an active agent within the core of body of the nanoparticles described herein. For example, in embodiments of the invention where the nanoparticles have a solid core, as defined above for micelles and cylindrical worms, then the active agent will be held within the polymer matrix of the nanoparticles in the core of said particles. Alternatively, in embodiments where the nanoparticles are in the form of vesicles, then the active agents may be held within the hollow core of the vesicle.

In embodiments of the invention, nanoparticulate compositions that further comprise an active agent may contain from 0.01 to 50 weight % of the active agent relative to the weight of the composition as a whole. For example, the active agent may be present in an amount of from 1 to 30 weight %, such as from 5 to 10 weight % relative to the weight of the composition as a whole.

For the avoidance of doubt, it is explicitly contemplated herein that the top and bottom values provided in a set of ranges in relation to a specific feature may be combined in any way to generate further ranges that are also explicitly contemplated. For example, with respect to the weight percentages provided above, the following ranges are to be considered as explicitly disclosed:

0.01 to 1 weight %, 0.01 to 5 weight %, 0.01 to 10 weight %, 0.01 to 30 weight %, 0.01 to 50 weight %;
1 to 5 weight %, 1 to 10 weight %, 1 to 30 weight %, 1 to 50 weight %;
5 to 10 weight %, 5 to 30 weight %, 5 to 50 weight %;
10 to 30 weight %, 10 to 50 weight %; and
30 to 50 weight %.

When used, herein the active agent may be selected from one or more of the group consisting of vitamin C, peptides, glycerol, dyes, flavours, perfume oils, citronellal, silicon oils, organosilicons, pesticides, Beta-carotene and a pharmacologically active agent.

The term "pharmacologically active agent" when used herein may refer to a substance useful for the treatment of or the prevention of a condition affecting a human or other animal. Said condition may be a disease, a disorder or a physiological condition. It will be appreciated that the active agent may not directly affect the underlying condition, but may be used as an adjuvant with a further active agent to enhance the effectiveness of the other active agent. Thus, the term "pharmacologically active agent" herein includes all classes of pharmacologically active agents, whether adjuvant or therapeutic, that may be provided to a subject through oral administration. When used herein, the term "pharmacologically active agent" and "drug" may be used interchangeably and so the term "drug" may be interpreted based on the definition of "active agent". Examples of pharmacologically active agents include, but are not limited to ibuprofen, fenofibrate, and isotrentinoin.

Further active agents that may be mentioned herein may include, but are not limited to, carbon metabolites (e.g. glucose, fructose, fumarate, etc.), electron acceptors (e.g. nitrate, peroxide, etc.), as well as a vitamin, such as vitamin A, B1, B2, B3, B6, B12, D, E, biotin, folate, and panothenate; minerals such as calcium, magnesium, selenium, and zinc; an amino acid such as asparagine, carnitine, glutamine, and serine; an antioxidant selected from coenzyme Q10, glutathione, and cysteine; or a metabolite such as lipoic acid, oleic add, choline, inositol, fructose, glucose, insulin, epigallocatechin gallate, and mixtures thereof.

As noted above, the nanoparticulate compositions may be a composition where some or all of the nanoparticles are in the form of a vesicle. When the nanoparticles are in the form of a vesicle, the amphipathic block copolymer may be arranged in the form of a membrane with an outer and inner surface, which inner surface defines a core region. This is analogous to a phospholipid cell membrane.

In embodiments of the invention, where some or all of the nanoparticles are in the form of a vesicle, said vesicle may have a core region that may comprise an active agent and/or aliquid. The nature of the active agent and liquid in the core will be determined by the nature of the nanoparticles that have been formed, as discussed in more detail below. Vesicles that may be mentioned herein may be nanoparticles having an average diameter of from 100 to 500 nm.

For example, the amphipathic block copolymer may be arranged so that the outer and inner surface of the membrane are formed from the hydrophilic blocks of the copolymer. In such vesicles, the amphipathic block copolymer may have an average ratio of hydrophobic repeating units to hydrophilic repeating units of from 1:9 to at least 9:1, such as from 1:1 to 5000:1, such as from 4:1 to 2000:1, such as from 9:1 to 1000:1. Vesicles of this type may be particularly suited to encapsulating hydrophilic active agents and polar liquids in the core of the vesicle.

For example, in vesicles where the amphipathic block copolymer may be arranged so that the outer and inner surface of the membrane are formed from the hydrophilic blocks of the copolymer, a hydrophilic active agent may be substantially (e.g. ≥90 wt %, such as ≥95 wt %, such as ≥99.9 wt %) encapsulated in the core region of the vesicle. Examples of hydrophilic active agents include, but are not limited to vitamin C, peptides, glycerol, dyes and flavours.

In addition or in place of the hydrophilic active agent, the composition may further comprise a polar liquid that is encapsulated in the core region of the vesicle. For example, the polar liquid may consist of one or more of the group consisting of water, a $C_{1-6}$ monoalcohol, a $C_{3-6}$ ketone, a glycol, acetonitrile, an amide, and a sulfoxide.

Examples of $C_{1-6}$ monoalcohols include, but are not limited to, ethanol, methanol, propanol, isopropanol, and butanol. Examples of $C_{3-6}$ ketones include, but are not limited to, acetone. Examples of glycols include, but are not limited to, ethylene glycols and polyethylene glycols. Examples of amides include, but are not limited to, dimethylformamide. Examples of sulfoxides include, but are not limited to, dimethylsulfoxide.

In alternative or additional embodiments of such vesicles (where the surfaces are formed from hydrophilic copolymer blocks), the composition may further comprise a hydrophobic active agent that is substantially (e.g. ≥90 wt %, such as 95 wt %, such as ≥99.9 wt %) encapsulated in the membrane of the vesicle. Examples of hydrophobic active agents include, but are not limited to, perfume oils, citronellal, silicon oils, organosilicons, pesticides, ibuprofen, fenofibrate, isotrentinoin and beta-carotene.

As will be appreciated, the polarity of the copolymeric blocks can be reversed, such that the amphipathic block copolymer may be arranged so that the outer and inner surface of the membrane are formed from the hydrophobic blocks of the copolymer. In such vesicles, the amphipathic block copolymer may have an average ratio of hydrophilic repeating units to hydrophobic repeating units of from 1:9 to at least 9:1, such as from 1:1 to 5000:1, such as from 4:1 to 2000:1, such as from 9:1 to 1000:1. Vesicles of this type may be particularly suited to encapsulating hydrophobic active agents and non-polar liquids in the core of the vesicle.

For example, in vesicles where the amphipathic block copolymer may be arranged so that the outer and inner surface of the membrane are formed from the hydrophobic blocks of the copolymer, a hydrophobic active agent may be substantially (e.g. ≥90 wt %, such as ≥95 wt %, such as ≥99.9 wt %) encapsulated in the core region of the vesicle. Examples of hydrophobic active agents include, but are not limited to perfume oils, citronellal, silicon oils, organosilicons, pesticides, ibuprofen, fenofibrate, isotrentinoin and beta-carotene. In addition or in place of the hydrophobic active agent, the composition may further comprise a non-polar liquid that is encapsulated in the core region of the vesicle. For example, the non-polar liquid consists of one or more of the group consisting of a $C_{5-10}$ alkane, a $C_{5-10}$ alkene, a $C_{5-10}$ alkyne, and a $C_{6-10}$ arene, where said non-polar liquids are unsubstituted or substituted by one or more halogen atoms.

Examples of $C_{5-10}$ alkanes include, but are not limited to, hexane. Examples of $C_{5-10}$ alkenes include, but are not limited to, hexene. Examples of $C_{5-10}$ alkynes include, but are not limited to, hexyne. Examples of $C_{6-10}$ arenes include, but are not limited to, benzene and toluene. In addition, the above-mentioned examples may be substituted by one or more halogen atoms (e.g. Br, Cl, I or, more particularly, F). Examples of such substituted compounds include, but are not limited to, hexafluorobenzene, and tetrahydrofuran.

In alternative or additional embodiments of such vesicles (where the surfaces are formed from hydrophilic copolymer blocks), the composition may further comprise a hydrophilic active agent that is substantially (e.g. ≥90 wt %, such as ≥95 wt %, such as ≥99.9 wt %) encapsulated in the membrane of the vesicle. Examples of hydrophilic active agents are provided hereinbefore.

In embodiments of the invention, where some or all of the nanoparticles are in the form of a micelle, said micelle may have a core region that may comprise an active agent. The nature of the active agent in the core will be determined by the nature of the nanoparticles that have been formed. For example, micelles formed such that the hydrophilic blocks of the amphipathic block copolymer are arranged on the surface of the nanoparticle may be suitable for the encapsulation of hydrophobic active agents (as described hereinbefore). Alternatively, micelles formed such that the hydrophobic blocks of the amphipathic block copolymer are arranged on the surface of the nanoparticle may be suitable for the encapsulation of hydrophilic active agents (as described hereinbefore). Micelles that may be mentioned herein may be nanoparticles having an average diameter of from 25 to 100 nm, such as from 28 to 80 nm.

For example, when the nanoparticles are in the form of a micelle, the amphipathic block copolymer may have an average ratio of hydrophobic repeating units to hydrophilic repeating units of from 1:100 to 10:1, such as from 1:10 to 10:1, such as from 1:1 to 5:1, such as from 1.8:1 to 4:1. In such materials, the hydrophobic repeating units will form the surface of the nanoparticles, with the hydrophilic repeating units forming the core. In embodiments that have the opposite arrangement, the amphipathic block copolymer may have an average ratio of hydrophilic repeating units to hydrophobic repeating units of from 1:100 to 10:1, such as from 1:10 to 10:1, such as from 1:1 to 5:1, such as from 1.8:1 to 4:1. In such materials, the hydrophilic repeating units will form the surface of the nanoparticles, with the hydrophobic repeating units forming the core.

In embodiments of the invention, where some or all of the nanoparticles are in the form of cylindrical worm structures, said cylindrical worm structures may have a core region that may comprise an active agent. The nature of the active agent in the core will be determined by the nature of the nanoparticles that have been formed. For example, cylindrical worm structures formed such that the hydrophilic blocks of the amphipathic block copolymer are arranged on the surface of the nanoparticle may be suitable for the encapsulation of hydrophobic active agents (as described hereinbefore). Alternatively, cylindrical worm structures formed such that the hydrophobic blocks of the amphipathic block copolymer are arranged on the surface of the nanoparticle may be suitable for the encapsulation of hydrophilic active agents (as described hereinbefore). Cylindrical worm structures that may be mentioned herein may be nanoparticles having an average diameter of from 50 to 200 nm, such as from 70 to 150 nm.

For example, when the nanoparticles are in the form of cylindrical worm structures, the amphipathic block copolymer may have an average ratio of hydrophobic repeating units to hydrophilic repeating units of from 1:1 to 100:1, such as from 4:1 to 9:1. In such materials, the hydrophobic repeating units will form the surface of the nanoparticles, with the hydrophilic repeating units forming the core. In embodiments that have the opposite arrangement, the amphipathic block copolymer may have an average ratio of hydrophilic repeating units to hydrophobic repeating units of from 1:1 to 100:1, such as from 4:1 to 9:1. In such materials, the hydrophilic repeating units will form the surface of the nanoparticles, with the hydrophobic repeating units forming the core.

The amphipathic block copolymer may be a poly(acrylic acid-co-acrylate ester) or a poly(polyethylene glycol ether methacrylate)-co-acrylate ester, optionally where the amphipathic block copolymer may be poly(methacrylic acid-co-methyl methacrylate) and/or poly((polyethylene glycol monomethyl ether methacrylate)-co-methyl methacrylate). In certain embodiments, the amphipathic block copolymer may be a poly(acrylic acid-co-acrylate ester), such as poly(methacrylic acid-co-methyl methacrylate).

In certain embodiments, the amphipathic block copolymer may be crosslinked to permanently stabilise the obtained assembly structures (micelles, worms, and vesicles) and hence to give them long term stability.

While it is possible to make compositions that only comprise one of micelles, cylindrical worm structures or vesicles, it is also possible to form compositions where any two or all three of these structures are formed. In preferred embodiments that may be mentioned herein, the compositions are formed from only one of micelles, cylindrical worm structures or vesicles or from mixtures of micelles and cylindrical worm structures or cylindrical worm structures and vesicles. When present in a mixture comprising any two of micelles, cylindrical worm structures or vesicles, the mixture may contain from 0.1 to 99.9 wt % of each type of nanoparticle (with the sum adding to 100 wt %). When present in a mixture comprising all three of micelles, cylindrical worm structures or vesicles, the mixture may contain from 0.05 to 99.9 wt % of each type of nanoparticle (with the sum adding to 100 wt %).

As will be appreciated, the current invention also relates to methods of making the above-mentioned nanoparticulate compositions. Thus, there is also disclosed a method of forming a nanoparticulate composition as described above using polymerisation induced self-assembly, the method comprising the step of forming a block copolymer by reacting a monomeric material with a macroinitiator compound in the presence of an initiator compound, a catalyst and a solvent, wherein:

if the monomeric material polymerises to provide a hydrophobic polymer block, then the macroinitiator compound is a hydrophilic polymer or oligomer or if the monomeric material polymerises to provide a hydrophilic block, then the macroinitiator compound is a hydrophobic polymer or oligomer;

the macroinitiator compound is terminated with a halogen atom;

the monomeric material, the macroinitiator compound, the initiator compound, the catalyst and the solvent are all substantially free of compounds comprising sulfur; and the monomeric material, the macroinitiator compound, the initiator compound, the catalyst and the solvent are all substantially free of a heavy metal.

The method disclosed above does not make use of heavy metals and/or sulfur as either part of a catalyst or as a reactant/reagent. As such, the compositions produced are either completely free of sulfur and heavy metals or contain a substantially reduced amount of said materials relative to compostions made using other methods.

Any suitable catalyst may be used in the method disclosed herein. For example, the catalyst may be a metal halide, where the halogen atom of the macroinitiator compound and the halide atom have the same atomic number and the metal may be selected from sodium, potassium, magnesium, and calcium. For example, the metal in the metal halide may be selected from sodium or potassium. In particular embodiments, the metal halide used as a catalyst may be sodium iodide and/or the halogen atom in the macroinitiator compound may be iodine.

Any suitable initiator compound may be used in the method disclosed herein. For example, the initiator compound may be an azo initiator, such as 2,2'-azobis(2,4-dimethylvaleronitrile).

The macroinitiator compound used herein may contain a suitable number of repeating units. For example, the macroinitiator compound may contain an average of from 1 to 1000 repeating units, such as from 5 to 100 repeating units, such as from 10 to 20 repeating units.

In certain embodiments of the invention, the monomeric material may be an acrylate ester (e.g. methyl methacrylate), and the macroinitiator may be a poly(acrylic acid) or an oligo(acrylic acid) (e.g. poly(methylacrylic acid) or an oligo(methacrylic acid)). In such embodiments, the solvent used for conducting the method may be a polar solvent. Examples of suitable polar solvents include, but are not limited to, water, a $C_{1-6}$ monoalcohol, a $C_{3-6}$ ketone, a glycol, acetonitrile, an amide, and a sulfoxide.

Examples of $C_{1-6}$ monoalcohols include, but are not limited to, ethanol, methanol, propanol, isopropanol, and butanol. Examples of $C_{3-6}$ ketones include, but are not limited to, acetone. Examples of glycols include, but are not limited to, ethylene glycols and polyethylene glycols. Examples of amides include, but are not limited to, dimethylformamide. Examples of sulfoxides include, but are not limited to, dimethylsulfoxide.

In embodiments of the invention where the macroinitiator may be a poly(acrylic acid) or an oligo(acrylic acid), the macroinitiator compound may have the formula I:

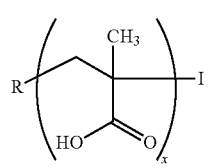

I where x is from 1 to 1000, such as from 5 to 100, such as from 10 to 20; and R is a branched or unbranched $C_{1-10}$ alkyl group that is unsubstituted or substituted by one or more of CN, aryl and $CO_2R'$, wherein R' is H or $C_{1-6}$ a alkyl group, optionally wherein R is —$CH(CH_3)_2CN$.

The term "aryl" when used herein includes $C_{6-14}$ (such as $C_{6-13}$ (e.g. $C_{6-10}$)) aryl groups. Such groups may be monocyclic, bicyclic or tricyclic and have between 6 and 14 ring carbon atoms, in which at least one ring is aromatic. The point of attachment of aryl groups may be via any atom of the ring system. However, when aryl groups are bicyclic or tricyclic, they are linked to the rest of the molecule via an aromatic ring. $C_{6-10}$ aryl groups include phenyl, naphthyl and the like, such as 1,2,3,4-tetrahydronaphthyl, indanyl, indenyl and fluorenyl. Embodiments of the invention that may be mentioned include those in which aryl is phenyl.

In alternative embodiments of the invention, the monomeric material may be an acrylic acid (e.g. methacrylic acid) and the macroinitiator compound may be a poly(acrylate ester) or an oligo(acrylate ester), such as poly(methacrylate) or oligo(methacrylate). In such embodiments, the solvent may be a non-polar solvent. Examples of suitable non-polar solvents include, but are not limited to, $C_{5-10}$ alkane, a $C_{5-10}$ alkene, a $C_{5-10}$ alkyne, and a $C_{6-10}$ arene, where said non-polar liquids are unsubstituted or substituted by one or more halogen atoms.

Examples of $C_{5-10}$ alkanes include, but are not limited to, hexane. Examples of $C_{5-10}$ alkenes include, but are not limited to, hexene. Examples of $C_{5-10}$ alkynes include, but are not limited to, hexyne. Examples of $C_{6-10}$ arenes include, but are not limited to, benzene and toluene. In addition, the above-mentioned examples may be substituted by one or more halogen atoms (e.g. Br, Cl, I or, more particularly, F). Examples of such substituted compounds include, but are not limited to, hexafluorobenzene, and tetrahydrofuran.

In embodiments of the invention where the macroinitiator may be a poly(acrylate ester) or an oligo(acrylate ester), the macroinitiator compound may have the formula II:

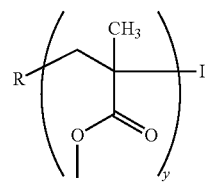

II where y is from 1 to 1000, such as from 5 to 100, such as from 10 to 20; and R is a branched or unbranched $C_{1-10}$ alkyl group that is unsubstituted or substituted by one or more of CN, aryl and $CO_2R'$, wherein R' is H or a $C_{1-6}$ alkyl group, optionally wherein R is —$CH(CH_3)_2CN$.

In the methods described above:
(a) the molar ratio of monomeric material to macroinitiator compound in the solvent is from 30:1 to 500:1, such as from 50:1 to 300:1; and/or
(b) the molar ratio of monomeric material to catalyst in the solvent is from 150:1 to 300:1, such as from 190:1 to 200:1; and/or
(c) the molar ratio of monomeric material to initiator in the solvent is from 150:1 to 300:1, such as from 190:1 to 200:1. For the avoidance of doubt, these are generic features that may be shared between any of the embodiments described hereinbefore.

In certain embodiments, the step of forming a block copolymer may be conducted in the presence of a crosslinking agent. Any suitable crosslinking agent may be used. Examples of suitable crosslinking agents include, but are not limited to, an ethylene glycol diacrylate ester (e.g. ethylene glycol dimethyacrylate) when the monomeric material is an acrylate ester or an ethylene glycol diacrylic acid (e.g. ethylene glycol dimethacrylic acid) when the monomeric material is an acrylic acid. In embodiments where a crosslinking agent is present, the molar ratio of monomeric material to crosslinking agent in the solvent may be from 10:1 to 50:1, such as from 20:1 to 40:1.

In certain embodiments of the invention, the step of forming a block copolymer may be conducted in the presence of an active agent. This allows for the convenient formation of the composition. In such embodiments, the molar ratio of monomeric material to active agent in the solvent may be from 1:1 to 300:1, such as from 100:1 to 250:1, such as from 150:1 to 225:1, such as from 190:1 to 200:1. However, this method may not be suitable for all potential active agents (e.g. peptides). For such active agents (peptides) the active agent may be conveniently encapsulated after the nanoparticle has been formed by osmosis, using standard techniques.

The active agents described hereinbefore may be incorporated using the methods described above. It will be appreciated that the methods described above may provide particles having shells/surfaces that are hydrophilic or hydrophobic in nature and the active agents that may be deposited in the relevant compartments are discussed hereinbefore in relation to the final products and so will not be repeated here.

The method described above may be used to obtain nanoparticles in the form of vesicles under suitable conditions (whether only vesicles or in a mixture with micelles and cylindrical worm structures or vesicles and cylindrical worm structures). Suitable conditions include those in which the molar ratio of monomeric material to macroinitiator compound in the solvent is from 100:1 to 500:1, such as from 110:1 to 300:1 and the reaction is allowed to occur for a period of time such that an average ratio of monomeric material repeating units to macroinitiator repeating units from 1:9 to at least 9:1, such as from 1:1 to 5000:1, such as from 4:1 to 2000:1, such as from 9:1 to 1000:1 is obtained.

The method described above may be used to obtain nanoparticles in the form of micelles under suitable conditions (whether only micelles or in a mixture with vesicles and cylindrical worm structures or micelles and cylindrical worm structures). Suitable conditions include those in which the molar ratio of monomeric material to macroinitiator compound in the solvent is from 40:1 to 100:1, such as from 60:1 to 90:1 and the reaction is allowed to occur for a period of time such that an average ratio of monomeric material repeating units to macroinitiator repeating units is from 1:100 to 10:1, such as from 1:10 to 10:1, such as from 1:1 to 5:1, such as from 1.8:1 to 4:1 is obtained.

The method described above may be used to obtain nanoparticles in the form of cylindrical worm structures under suitable conditions (whether only cylindrical worm structures or in a mixture with vesicles and micelles, micelles and cylindrical worm structures or vesicles and cylindrical worm structures). Suitable conditions include those in which the molar ratio of monomeric material to macroinitiator compound in the solvent is from 40:1 to 200:1, such as from 60:1 to 150:1 and the reaction is allowed to occur for a period of time such that an average ratio of monomeric material repeating units to macroinitiator repeating units is from 1:1 to 100:1, such as from 4:1 to 9:1 is obtained.

The macroinitiator compound used in the methods described herein may be formed by polymerising a monomeric material with a dormant initiator compound in the presence of an initiator compound, a catalyst and a solvent, wherein
the dormant initiator compound is a hydrocarbon comprising a halogen atom;
the monomeric material, the dormant initiator compound, the initiator compound, the catalyst and the solvent are all substantially free of compounds comprising sulfur; and
the monomeric material, the dormant initiator compound, the initiator compound, the catalyst and the solvent are all substantially free of a heavy metal.

Any suitable catalyst may be used in this macroinitiator formation method. For example, the metal halides described above to form the nanoparticulate composition may be used. For example, the metal halide may be sodium iodide and the halogen atom in the dormant initiator compound may be iodine. The initiator used in this macroinitiator formation method may be the same as used to form the nanoparticulate composition, as described above. That is, the initiator compound may be an azo initiator, such as is 2,2'-azobis(2,4-dimethylvaleronitrile).

In certain embodiments that may be described herein, the macroinitiator may contain an average of from 1 to 1000 repeating units, such as from 5 to 100 repeating units, such as from to 20 repeating units.

Any suitable substance may be used as the dormant initiator compound. Examples of a suitable dormant initiator compound include, but are not limited to, 2-iodo-2-methylpropionitrile.

The invention will now be described with reference to the following non-limiting examples.

EXAMPLES

Materials

Methyl methacrylate (MMA) (>99.8%, Tokyo Chemical Industry (TCI), Japan), methacrylic acid (MAA) (>99%, TCI), ethylene glycol dimethacrylate (EGDMA) (98%, Sigma Aldrich), iodo-2-methylpropionitrile (CP-I) (>95%, TCI), NaI (>99.5%, Kanto), 2,2'-azobis(2,4-dimethyl valeronitrile) (V65) (95%, Wako Pure Chemical, Japan), and trimethylsilyldiazomethane (10% in hexane) (TCI) were used as received.

Analytical Methods

For the gel permeation chromatography (GPC) analysis, PMAA-1 and PMAA-PMMA-1 were methylated prior to the analysis (L. Couvreur, et al., *Macromolecules*, 2003, 36, 8260-8267). PMAA-1 (purified by reprecipitation) (15 mg) or PMAA-PMMA-1 (not purified but dried after the polymerization) (15 mg) was first dissolved in tetrahydrofuran (THF) (1 mL). Trimethylsilyl)diazomethane (1.5 equivalents to the COOH group) was added into the solution. The solution was stirred overnight at room temperature and analysed with GPC. The GPC analysis was performed on a Shodex GPC-101 liquid chromatograph (Tokyo, Japan) equipped with two Shodex KF-804L mixed gel columns (300×8.0 mm; bead size=7 μm; pore size=20-200 Å). The eluent was THF at a flow rate of 1.0 mL/min. Sample detection was conducted using a Shodex differential refractometer RI-101. The column system was calibrated with standard poly(methyl methacrylate)s (PMMAs).

The NMR spectra were recorded on a Bruker (Germany) AV500 spectrometer (500 MHz) and Bruker BBFO400 spectrometer (400 MHz) at ambient temperature. DMSO-$d_6$ (Cambridge Isotope Laboratories (CIL), USA) and $D_2O$ (CIL) were used as the solvents for the NMR analysis.

Transmission electron microscopy (TEM) images were obtained on a JEM-1400 transmission electron microscope (JEOL, Japan) operated at 100 kV. The TEM grid was carbon-coated on 200 mesh (copper) (Ted Pella, USA). The cryogenic TEM (cryo-TEM) image was obtained in a FEI Titan Krios transmission electron microscope equipped with an auto sampler and a field emission gun (FEG) and performed under 300 kV. The image was captured with a Falcon II camera (4*4) with magnification of 29,000 and a pixel size of 2.873 Å. The vitrification of the sample was performed using a vitrification robot (FEI Vitrobot Mark IV, Hillsboro, OR, USA). A 5 µL stock solution was added on a grid (Quantifoil, R2/2, Holey Carbon film) which was freshly glow-discharged before use at 20 mA for 60 s. An excess sample was blotted away with a filter paper at room temperature, in 100% humidity, in a blotting time of 2 s, and with a blotting force of 1. Then it was vitrified in liquid ethane and immediately transferred to a cryo-holder.

The dynamic light scattering (DLS) measurement was carried out on a Malvern Zetasizer Nano ZSP (Worcestershire, UK). The test angle for the DLS analysis was 173° (backscattering detection). Water was used as the solvent.

Example 1. Synthesis and Characterisation of $PMAA_{20}$-$PMMA_{180}$ Block Copolymer by NTMC-CRP and PISA (Via NTMC-CRP)

The $PMAA_x$-$PMMA_y$ block copolymer of the current invention was synthesised by a combination of two processes sequentially (where x represents the DP of PMAA and y represents the DP of PMMA). The PMAA-I macroinitiators were first synthesised by non-transition-metal catalysed controlled radical polymerisation (NTMC-CRP), which were then subsequently reacted with MMA monomers in polymerisation-induced self-assembly (PISA) to form the PMAA-PMMA block copolymer. In this specific example, $PMAA_{20}$-$PMMA_{180}$ was synthesised.

Synthesis of PMAA-I Macroinitiators by NTMC-CRP
Experimental Procedures

Figure 1:
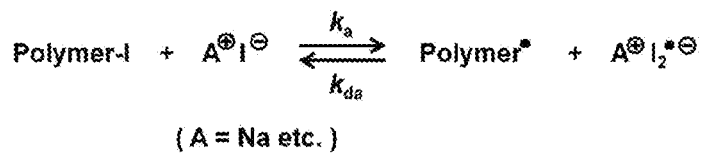
Figure 1:
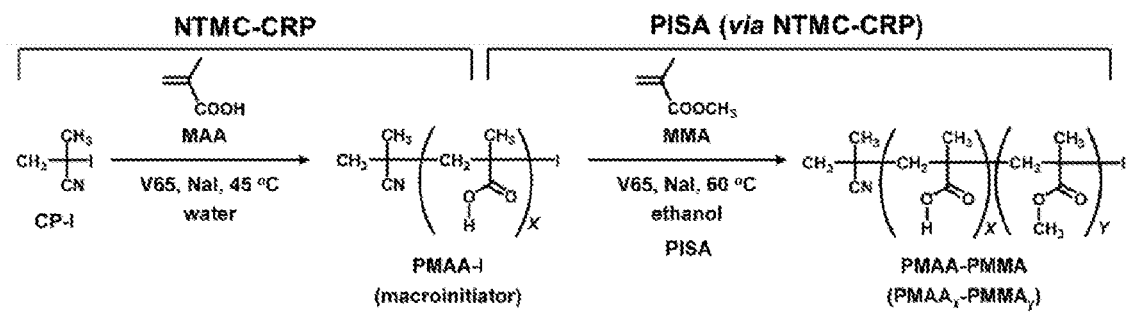

PMAA-I hydrophilic macroinitiators were prepared using NaI-catalysed NTMC-CRP (FIG. 1a). Typically, a mixture of methacrylic acid (MAA) (50 eq., monomer), 2-iodo-2-methylpropionitrile (CP-I) (1 eq., initiating dormant species), 2,2'-azobis(2,4-dimethylvaleronitrile) (V65) (1.67 eq., azo initiator), NaI (1 eq., catalyst), and water (50 wt %, solvent) was heated at 45° C. for 1.2 h (FIG. 1b and Table 1, entry 1). The polymerisation was intentionally stopped at a low monomer conversion (26%) for a short time (1.2 h) to retain iodides at the chain end. The high iodide-chain-end fidelity of the macroinitiator was demonstrated by the high block efficiency as shown below. The obtained macroinitiator was purified by reprecipitation in diethyl ether (non-solvent). Polymers with various degrees of polymerisation (DP) can be obtained by varying the reaction time.

In one specific example, a mixture (2 g) of MAA (8 M), CP-I (160 mM), V65 (266 mM), NaI (160 mM), and water (50 wt % of the mixture) was heated in a Schlenk flask at 45° C. under argon atmosphere with magnetic stirring. The reaction mixture was diluted with 1 mL ethanol. The polymer was reprecipitated in diethyl ether and dried under vacuum.

Characterisation

The as-synthesised PMAA-I polymer was first methylated with trimethylsilyldiazomethane to form PMMA-I, prior to characterisation by GPC using THF as an eluent. A PMAA-I with $M_n$=1700 (DP=20) and PDI=1.15 (after the purification) was obtained, where $M_n$ is the number-average molecular weight, DP is the degree of polymerisation and PDI is the polydispersity index. Similarly, PMAA-I polymers with DP=11 and 5 were also obtained using a reaction time of 0.7 h and 0.5 h respectively (Table 1, entries 2 and 3). These PMAA-I polymers were used as hydrophilic macroinitiators in the following PISA experiments.

TABLE 1

Synthesis of PMAA-I macroinitiators with various DP.

| Entry | $[MAA]_0/[CP-I]_0/[V65]_0/[NaI]_0$ (mM)$^a$ | T (° C.) | t (h) | Conv. (%) | $M_n^b$ | $DP^b$ | $PDI^b$ |
|---|---|---|---|---|---|---|---|
| 1 | 8000/160/266/160 | 45 | 1.2 | 26 | 1700 | 20 | 1.15 |
| 2 | 8000/160/266/160 | 45 | 0.7 | 15 | 900 | 11 | 1.12 |
| 3 | 8000/160/266/160 | 45 | 0.5 | 11 | 400 | 5 | 1.12 |

$^a$Solution polymerisation in 50 wt % water (solvent).
$^b$The $M_n$, DP, and PDI values of PMAA-I determined after purification (reprecipitation). PMAA-I was methylated to form PMMA-I, which was analysed with GPC using THF as the eluent. The $M_n$ values (e.g. 1700 in entry 1) for PMAA-I were calculated from those (e.g. 2000 in entry 1) determined for PMMA-I, considering the molecular weights of MAA (86) and MMA (100) monomer units.

Synthesis of $PMAA_{20}$-$PMMA_{180}$ block copolymer by PISA (via NTMC-CRP)
Experimental Procedures For the PISA reaction, methyl methacrylate (MMA) was chosen as the hydrophobic monomer and ethanol was chosen as the solvent. Typically, to synthesise $PMAA_{20}$-$PMMA_{180}$, a mixture of MMA (300 eq.), PMAA-I (DP=20) (1 eq., macroinitiator), V65 (1.5 eq., azo initiator), NaI (1.5 eq., catalyst) and ethanol was heated at 60° C. for 14 h (FIG. 1b and Table 2, entry 11). The amount of solvent used was 90 wt %, while the total amount of the macroinitiator and monomer was 10 wt % (macroinitiator/monomer=0.5/9.5). The solid content was to be 10% after a full (100%) conversion of MMA.

In an optimised reaction, a mixture (1.5 g) of MMA (8 M), PMAA-I (DP=20, 27 mM), NaI (40 mM), V65 (40 mM), and ethanol (90 wt % of the mixture) was heated in a Schlenk flask at 60° C. under argon atmosphere with magnetic stirring. After the prescribed time t, an aqueous solution (50 µL) of $NaHCO_3$ (0.9 equivalents to the COOH group) was added to the reaction mixture. An aliquot (0.1 mL) of the solution was dried under vacuum, methylated, and analysed with GPC. Another aliquot (0.1 mL) was diluted with DMSO-de (0.9 mL) and analysed with $^1H$ NMR for obtaining the monomer conversion. Another aliquot (0.1 mL) was diluted with an aqueous solution (0.5 mL) of KCl (1 mM), which then formed the stock solution. The stock solution (50 μL) was further diluted with water (0.6 mL) and analysed by DLS. The stock solution (10 μL) was also dropped on a TEM grid, dried under vacuum, and analysed by TEM.

The addition of $NaHCO_3$ and KCl stabilised the self-assemblies and prevented their aggregation upon storage at room temperature. Without this treatment, after cooling from the reaction temperature of 60° C., the self-assemblies gradually aggregated and precipitated. This treatment was required due to the nature of the PMAA-PMMA polymer, but may not be required for other types of polymers synthesised by this method.

Characterisation

It was observed from the GPC curves that a large fraction of the macroinitiator chains smoothly extended to block copolymers, indicating high block-efficiency (FIG. 2a). Further, the polymerisation reached a high monomer conversion (i.e. 75%) at 14 h (FIG. 2b). The $M_n$ increased with the monomer conversion, and the PDI was 1.14-1.40 (FIG. 2c). These results demonstrate the good livingness of this polymerisation. A deviation of $M_n$ at the later stage of polymerisation was ascribed to an increase number of chains originating from V65 (azo initiator). After 14 h, the self-assemblies of the polymer were generated, because the PMMA segment became long enough to be insoluble in ethanol.

At 14 h, $PMAA_{20}$-$PMMA_{180}$ (with 180 DP of PMMA) was generated and self-assembled to vesicles, as shown by the TEM image (FIG. 2d). The TEM sample was prepared by dropping the solution on a TEM grid and drying it under vacuum. The TEM samples prepared from the original ethanol reaction solution (FIG. 2e) and the treated aqueous solution (FIG. 2d) were compared. No morphological differences were observed, which indicated that the aqueous treatment (using $NaHCO_3$ and KCl) did not affect the morphology of the self-assembled polymer.

The treated polymer sample was also frozen in liquid ethane and a cryogenic TEM (cryo-TEM) analysis was conducted. The cryo-TEM (in situfrozen sample) (FIG. 2f) and normal TEM (dried sample) (FIG. 2d) images showed similar morphologies, which implied that the morphology of the self-assembled polymer remained unchanged upon drying. These results support that the dry TEM images of the stock solutions (that are discussed in subsequent examples) are accurate representation of the actual assembled structures generated during the polymerisation process.

Although the expected morphologies were observed in both the TEM and cryo-TEM images, they do not represent the only morphologies in the system (as this could be partially due to sample preparation and/or morphological changes that may occur immediately after the reaction. A direct evidence was obtained as shown by the crosslinking experiments (as discussed in Example 3), in which the morphologies were fixed by crosslinking in situ during the polymerisation process. The crosslinking results supported that the morphologies (sphere, worm, and vesicle) observed with TEM below were the actual morphologies generated during the polymerisation process, and not generated during the aqueous treatment or the TEM sample preparation.

The dynamic light scattering (DLS) analysis shows that the hydrodynamic size (DLS peak top) of the assembly was 465 nm (Table 2, entry 11). The contour length of this block copolymer (200 units) was determined to be 50 nm. The assembly size of 465 nm was much larger than twice of the contour length (which is 100 nm), indicating that the assembly was not a micelle but a vesicle. Notably, the solid content was as high as 7.6 wt % (0.5 wt % from the original macroinitiator and 7.1 wt % from the PMMA segment generated in the polymerisation). Therefore, this indicated that the NTMC-CRP-PISA system successfully yielded nano-capsules at a high solid content.

Example 2. Synthesis and Characterisation of $PMAA_x$-$PMMA_y$ Block Copolymer (of Various x and y Values) and their Respective Morphologies The synthesis of $PMAA_x$-$PMMA_y$ block copolymer with various x and y values was carried out following the method described in Example 1. $PMAA_x$-$PMMA_y$ block copolymer of various lengths were achieved by varying the DP of the PMAA-I macroinitiators, the concentrations of MMA monomers to PMAA-I macroinitiators, and the reaction time (t), as listed in Table 2.

Figure 3:
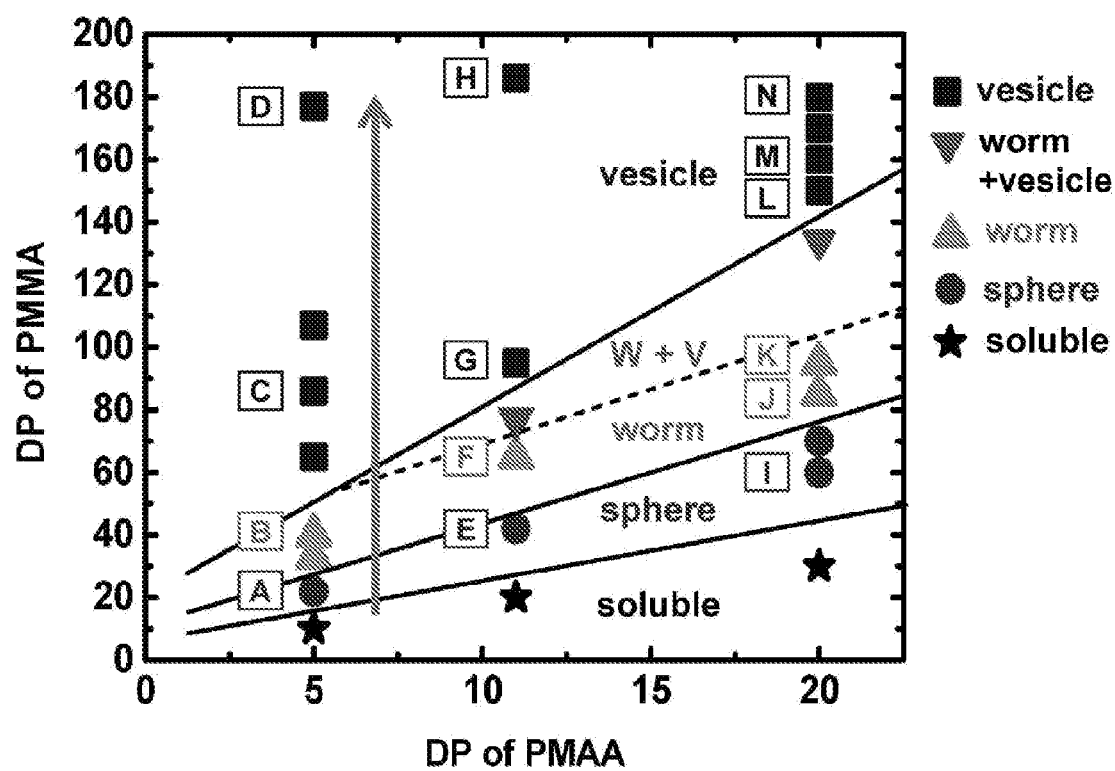
Figure 4:
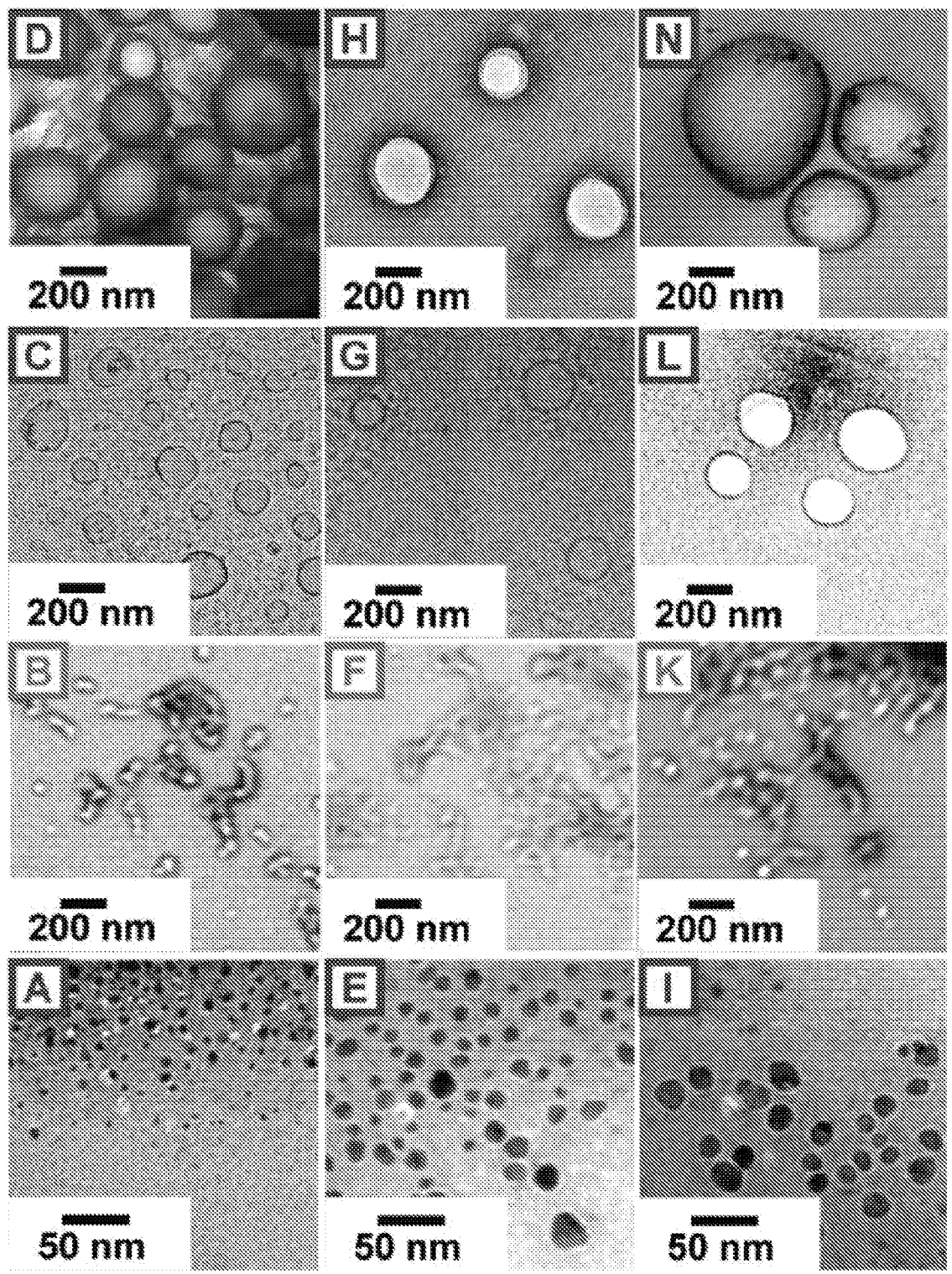

PMAA-I macroinitiators with three different DPs (5, 11, and 20) was used and the DP of the PMMA segment was varied from 0 to 193. A phase diagram depicting the morphologies of the various self-assembled polymers with various DP is as shown in FIG. 3, with the corresponding TEM images as shown in FIG. 4. We focused on high solid contents in this work. The solid content was 5-9 wt % in this diagram except for the soluble phase (2-5 wt % solid contents). The polymerisation conditions of MMA to generate the assemblies at >50% monomer conversions was optimised as shown in Table 2.

Using the $PMAA_5$-I macroinitiator with DP=5, a series of PISA experiments with varying of the DP of the PMMA segment (at DP of PMAA=5 in the horizontal axis in FIG. 3) was carried out.

The generated block copolymer was soluble for $PMAA_5$-$PMMA_{10}$ with a short PMMA segment of DP=10. As the DP of the PMMA segment increased, the block copolymer self-assembled to micelles (spheres) for $PMAA_5$-$PMMA_{22}$ (DP=22), worms for $PMAA_5$-$PMMA_{40}$ (DP=40), and vesicles for $PMAA_5$-$PMMA_{86}$ (DP=86) (FIG. 3). The assembly structure changed from micelles to worms to vesicles with an increase of the hydrophobic (PMMA) fraction, as illustrated in the TEM images (FIG. 4A-C). The hydrodynamic size of the sphere (28 nm) determined with DLS (Table 2, entry 1) was close to twice of the contour length of $PMAA_5$-$PMMA_{22}$ (15 nm), which was consistent with the sphere structure observed in the TEM image (FIG. 4A).

An increase in the DP of PMMA to 86 led to the assembly of vesicles with a larger hydrodynamic size of 184 nm (Table 2, entry 2). This size was much larger than twice of the contour length of $PMAA_5$-$PMMA_{86}$ (45 nm), which was consistent with the vesicle structure observed in the TEM image (FIG. 4C). A further increase in the DP of the PMMA segment to 177 ($PMAA_5$-$PMMA_{177}$) led to an increase in the vesicle size (440 nm) (Table 2, entry 4) and also an increase in the thickness of the shell, as observed in the TEM image (FIG. 4D). As such, nano-capsules with different sizes and different shell thickness were obtained.

Using the $PMAA_{11}$-I and $PMAA_{20}$-I macroinitiators with DP=11 and 20, the DP of the PMMA segment (FIG. 4E-N) was varied. The assembly structure changed from micelles to worms to vesicles with an increase of the hydrophobic fraction, similar to that observed with the $PMAA_5$-I macroinitiator with DP=5. The assembly structure is dependent on the fractions of the hydrophilic and hydrophobic segments in the block copolymer, which determined the curvature at the hydrophilic-hydrophobic interface. The structure is empirically related to the mass fraction. The fraction ($f_{PMMA}$) of the PMMA segment in the block copolymer is defined as $f_{PMMA}$=(DP of the PMMA segment)/(DP of the block copolymer). From the initial studies, the block copolymer was observed to be soluble with $f_{PMMA}$<0.65 and formed spheres with $f_{PMMA}$=0.65-0.8, worms with $f_{PMMA}$=0.8-0.9, and vesicles with $f_{PMMA}$>0.9. With further optimised studies, it was observed that the block copolymer was soluble with $f_{PMMA}$<0.75 and formed spheres with $f_{PMMA}$=0.75-0.85, worms with $f_{PMMA}$=0.85-0.9. The boundary between the phases may not be very sharp as there may be broad transition zones between the phases. This was supported by DLC size distribution index which tend to be larger at the boundary (Table 2). In addition, the size of the spheres, worms, and vesicles tend to be larger with an increase of the DP of the block copolymer. Given this, polymeric spheres (28-80 nm), worms (70-138 nm), and vesicles (154-493 nm, or 154-465 nm from subsequent optimised studies) of different sizes were obtained using the macroinitiators with different DPs (Table 2).

TABLE 2

Synthesis of PMMA$_x$-PMMA$_y$ by varying the DP of the PMAA-I macroinitiators, the concentrations of MMA monomers to PMAA-I macroinitiators, and the reaction time (t), in ethanol (90 wt %) at 60° C.

Figure 2:
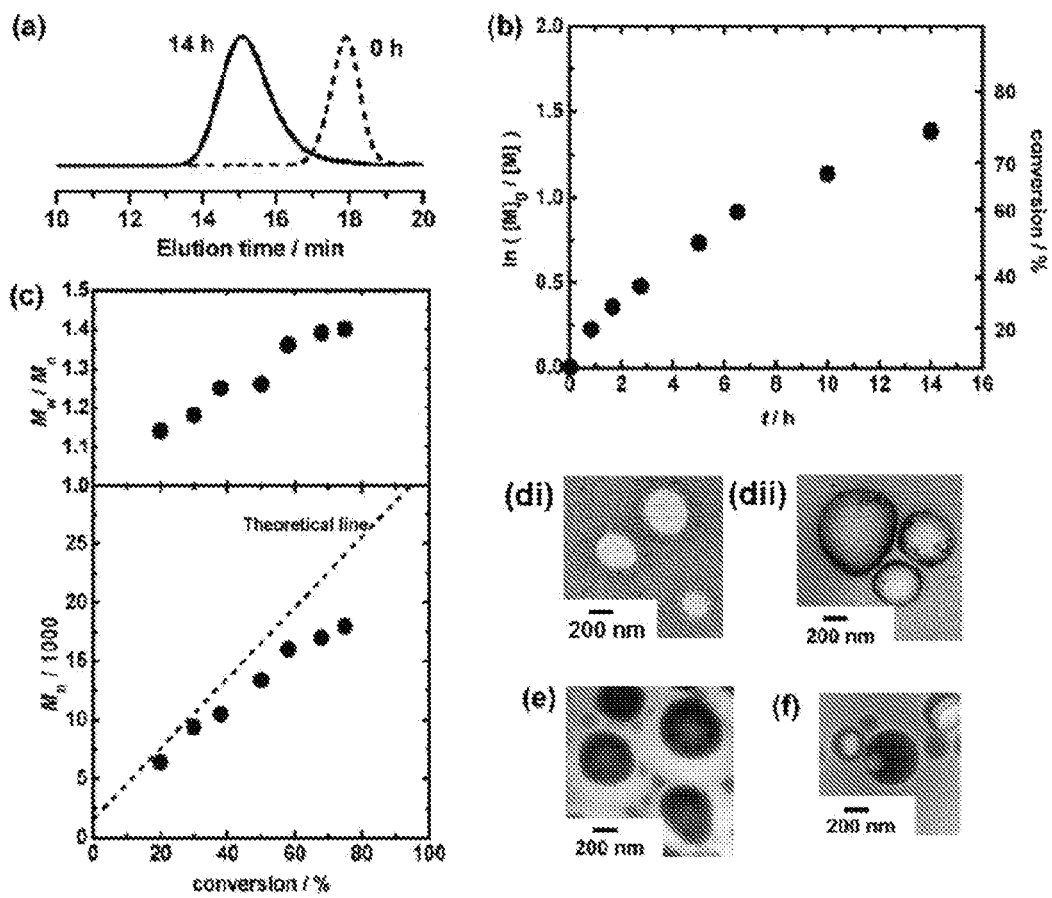

| Entry | DP of PMAA | [MMA]$_0$/ [PMAA-I]$_0$/ [NaI]$_0$/[V65]$_0$ (mM)[a] | t (h) | Conv (%) | DP of PMMA[b] | PDI[b] | Code of Block Copolymer | $f_{PMMA}$ inital | $f_{PMMA}$ final | Hydro-dynamic Diameter[c] (nm) | DLS Size Distribution Index | Assembled Structure[d] | Code in FIGS. 2 and 3 |
|---|---|---|---|---|---|---|---|---|---|---|---|---|---|
| 1 | 5 | 8000/133/40/40 | 0.3 | 30 | 10 | 1.10 | PMAA$_5$-PMMA$_{10}$ | 0.67 | 0.70 | — | — | Soluble | |
| | | | 0.6 | 50 | 22 | 1.10 | PMAA$_5$-PMMA$_{22}$ | 0.81 | 0.84 | 28 | 0.100 | S | A |
| | | | 1 | 64 | 33 | 1.32 | PMAA$_5$-PMMA$_{33}$ | 0.87 | 0.88 | 70 | 0.060 | W | |
| | | | 1.5 | 79 | 40 | 1.39 | PMAA$_5$-PMMA$_{40}$ | 0.89 | 0.90 | 106 | 0.080 | W | B |
| 2 | 5 | 8000/80/40/40 | 1.5 | 71 | 65 | 1.34 | PMAA$_5$-PMMA$_{65}$ | 0.93 | 0.94 | 154 | 0.060 | V | |
| | | | 2.5 | 80 | 86 | 1.39 | PMAA$_5$-PMMA$_{86}$ | 0.95 | 0.95 | 184 | 0.080 | V | C |
| 3 | 5 | 8000/53/40/40 | 3 | 69 | 107 | 1.49 | PMAA$_5$-PMMA$_{107}$ | 0.96 | 0.96 | 200 | 0.140 | V | |
| 4 | 5 | 8000/40/40/40 | 3 | 82 | 177 | 1.45 | PMAA$_5$-PMMA$_{177}$ | 0.98 | 0.98 | 440 | 0.220 | V | D |
| 5 | 11 | 8000/160/40/40 | 1 | 48 | 20 | 1.18 | PMAA$_{11}$-PMMA$_{20}$ | 0.65 | 0.68 | — | — | Soluble | |
| 6 | 11 | 8000/80/40/40 | 1.5 | 51 | 42 | 1.20 | PMAA$_{11}$-PMMA$_{42}$ | 0.79 | 0.82 | 43 | 0.105 | S | E |
| | | | 2 | 72 | 65 | 1.36 | PMAA$_{11}$-PMMA$_{65}$ | 0.86 | 0.87 | 138 | 0.120 | W | F |
| | | | 2.3 | 80 | 77 | 1.35 | PMAA$_{11}$-PMMA$_{77}$ | 0.88 | 0.89 | 159 | 0.176 | W + V | |
| 7 | 11 | 8000/53/40/40 | 3 | 70 | 95 | 1.41 | PMAA$_{11}$-PMMA$_{95}$ | 0.90 | 0.91 | 297 | 0.126 | V | G |
| | | | 6 | 83 | 186 | 1.40 | PMAA$_{11}$-PMMA$_{186}$ | 0.94 | 0.95 | 375 | 0.360 | V | H |
| 8 | 20 | 8000/80/40/40 | 1 | 34 | 30 | 1.10 | PMAA$_{20}$-PMMA$_{30}$ | 0.60 | 0.64 | — | — | Soluble | |
| | | | 1.6 | 58 | 60 | 1.25 | PMAA$_{20}$-PMMA$_{60}$ | 0.75 | 0.78 | 50 | 0.100 | S | I |
| | | | 2 | 68 | 70 | 1.34 | PMAA$_{20}$-PMMA$_{70}$ | 0.78 | 0.80 | 80 | 0.106 | S | |
| 9 | 20 | 8000/53/40/40 | 3.5 | 70 | 85 | 1.30 | PMAA$_{20}$-PMMA$_{85}$ | 0.81 | 0.83 | 110 | 0.268 | W | J |
| | | | 4 | 76 | 95 | 1.36 | PMAA$_{20}$-PMMA$_{95}$ | 0.83 | 0.85 | 121 | 0.200 | W | K |
| | | | 4.8 | 80 | 134 | 1.45 | PMAA$_{20}$-PMMA$_{134}$ | 0.87 | 0.89 | 150 | 0.215 | W + V | |
| 10 | 20 | 8000/40/40/40 | 5 | 73 | 150 | 1.43 | PMAA$_{20}$-PMMA$_{150}$ | 0.88 | 0.90 | 211 | 0.168 | V | L |
| | | | 5.2 | 82 | 160 | 1.44 | PMAA$_{20}$-PMMA$_{160}$ | 0.89 | 0.90 | 380 | 0.300 | V | M |
| 11 | 20 | 8000/27/40/40 | 10 | 68 | 170 | 1.39 | PMAA$_{20}$-PMMA$_{170}$ | 0.89 | 0.91 | 390 | 0.369 | V | |
| | | | 14 | 75 | 180 | 1.40 | PMAA$_{20}$-PMMA$_{180}$ | 0.90 | 0.91 | 465 | 0.450 | V | N |

[a]The mixture of MMA, PMAA-I, NaI, and V65 at the described concentration was diluted with ethanol (ethanol content = 90 wt %).
[b]DP and PDI were determined by THF-GPC after methylation of the PMAA segment.
[c]The DLS peak top value.
[d]S = sphere, W = worm, and V = vesicle.

Example 3. Synthesis of Fixed PMAA$_x$-(PMMA/EGDMA)$_y$ Block Copolymer, and Comparison of its Stability in Basic Conditions with PMAA$_x$-PMMA$_y$ Synthesis of PMAA$_x$-(PMMA/EGDMA)$_y$.

In Examples 1 and 2, a non-crosslinkable monomer MMA was used in the second block, which gave assembly structures that were not fixed. To fix the assembly structures, a cross-linkable divinyl monomer, i.e. ethylene glycol dimethacrylate (EGDMA), was used as a co-monomer with MMA (instead of MMA alone) in the second block in this example.

Figure 6:
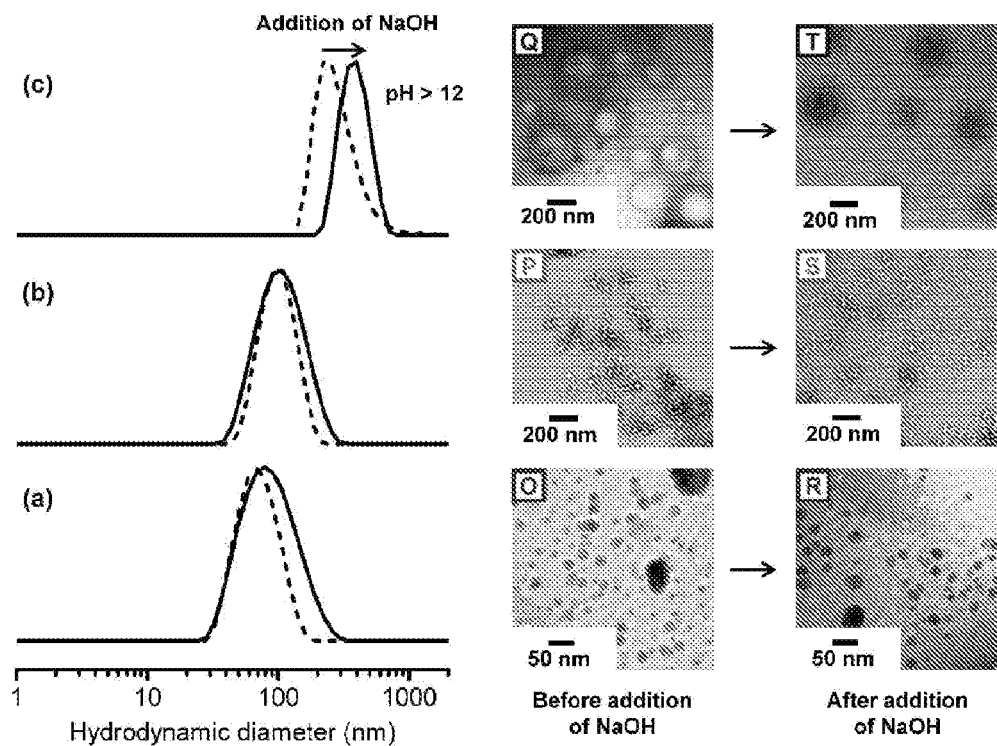

With that, the synthesis of PMAA$_x$-(PMMA/EGDMA)$_y$ block copolymer with various x and y values was carried out following the method described in Examples 1 and 2, and as listed in Table 3. Relatively small molar fractions (2.5-4.8% in initial studies, or 4.8-9.1% in optimised studies) of EGDMA were used in order for the crosslinking to take place after the assembly structures are generated. The EGDMA fraction was set smaller in the order of spheres (4.8% in initial studies, or 9.1% in optimised studies), worms (3.4% in initial studies, or 6.5% in optimised studies), and vesicles (2.5% in initial studies, or 4.8% in optimised studies) to delay the crosslinking point at a larger DP of the second segment. FIG. 6 shows the TEM images of spheres with PMAA$_{20}$-(PMMA/PEGDMA)$_{60}$ (part O), worms with PMAA$_{20}$-(PMMA/PEGDMA)$_{85}$ (part P), and vesicles with PMAA$_{20}$-(PMMA/PEGDMA)$_{160}$ (part Q).

Comparison of the Stability of PMAA$_x$-(PMMA/EGDMA)$_y$ with PMAA$_x$-PMMA$_y$ in Basic Condition In Example 2, using the PMAA$_{20}$-I macroinitiator with DP=20, spheres, worms and vesicles were obtained for PMAA$_{20}$-PMMA$_{60}$, PMAA$_{20}$-PMMA$_{85}$ and PMAA$_{20}$-PMMA$_{160}$, respectively. These assemblies decomposed in a strongly basic condition (pH>12) with sodium hydroxide (NaOH). The DLS analysis (FIG. 5a-c) showed that the spheres (50 nm), worms (110 nm), and vesicles (380 nm) decomposed to single polymer chains (2, 3, and 5 nm, respectively) in the basic condition.

The crosslinked assemblies were treated in a basic condition (pH>12) with NaOH. Unlike the non-crosslinked assemblies, the crosslinked assemblies did not decompose in the basic condition, as shown in the DLS analysis (FIG. 6a-c). With this basic treatment, the hydrodynamic size became slightly larger from 73 nm to 79 nm for the sphere, from 102 nm to 106 nm for the worms, and from 400 nm to 470 nm for vesicles (Table 3). This was due to the deprotonation of the carboxylic acid to the ionic form (carboxylate) and the PMAA segment became extended due to the electronic repulsion. The TEM images of the assemblies (after the addition of NaOH) showed no change in morphologies with the basic treatment (FIG. 6R-T). From the TEM image of the vesicles, it was observed that the shell of the vesicle was dark before the basic treatment (FIG. 6Q), the interior of the vesicle was dark after the basic treatment (FIG. 6T). This was due to the incorporation of NaOH (sodium ion) within the interior of the vesicles with the basic treatment, therefore, giving the opposite contrast.

Figure 5:
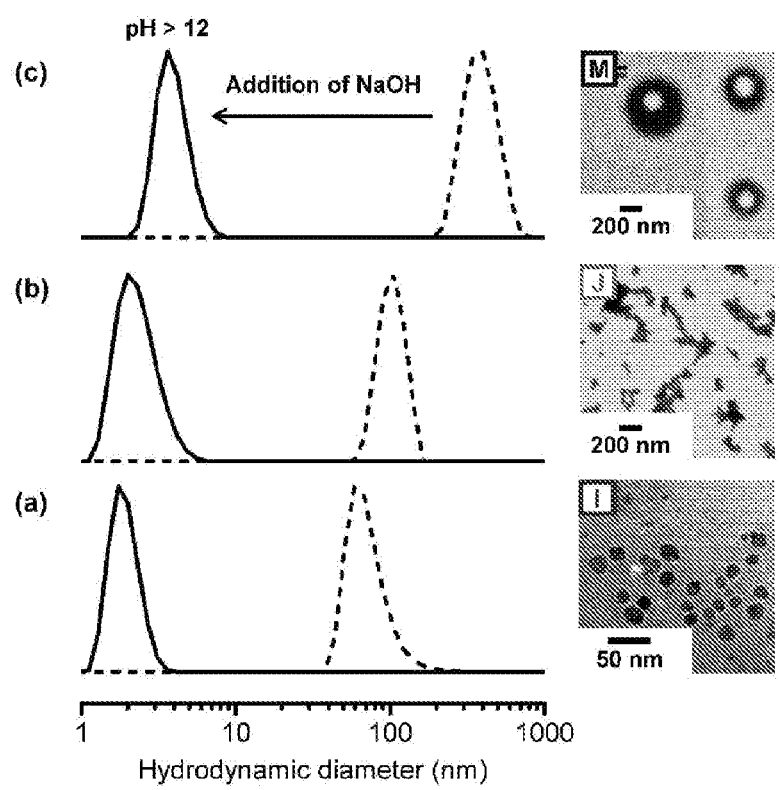

Importantly, the morphologies (sphere, worm, and vesicle) observed from the TEM images were the same with (FIG. 6) and without crosslinking (FIG. 5). For the crosslinking systems, the morphologies that were generated in situ during the polymerisation were fixed. This result clearly confirms that the morphologies discussed in Examples 1 and 2 for the non-crosslinked were also the actual structures generated during the polymerisation but not generated during the TEM sample preparation. From this study, it can be confirmed that the stable (fixed) assemblies were obtained.

TABLE 3

Synthesis of PMAA$_x$-(PMMA/PEGDMA)$_y$ in ethanol (90 wt %) at 60° C.

| Entry | [MMA]$_0$/[EGDMA]$_0$/ [PMAA$_{20}$-I]$_0$/[V65]$_0$/ [NaI]$_0$ (mM)$^a$ (subsequent, optimised values) | t (h) | Code of Block Copolymer$^b$ | DLS Hydrodynamic Diameter (nm)$^c$ | DLS Size Distribution Index | Assembled Structure$^d$ | Code in FIG. 6 |
|---|---|---|---|---|---|---|---|
| 1 | 7620/380/80/40/40 (7270/730/80/40/40) | 1.5 | PMAA$_{20}$-(PMMA/PEGDMA)$_{60}$ | 73 | 0.100 | S | O |
|   | after adding aqueous NaOH | — |   | 79 | 0.164 | S | R |
| 2 | 7730/270/53/40/40 (7480/520/53/40/40) | 3.5 | PMAA$_{20}$-(PMMA/PEGDMA)$_{85}$ | 102 | 0.143 | W | P |
|   | after adding aqueous NaOH | — |   | 106 | 0.108 | W | S |
| 3 | 7800/200/40/40/40 (7620/380/40/40/40) | 5.2 | PMAA$_{20}$-(PMMA/PEGDMA)$_{160}$ | 400 | 0.400 | V | Q |
|   | after adding aqueous NaOH | — |   | 470 | 0.414 | V | T |

$^a$The mixture of MMA, EGDMA, PMAA20-I, NaI, and V65 at the described concentration was diluted with ethanol (ethanol content = 90 wt %). The subsequent, optimised concentrations are as shown in the brackets.
$^b$DP of (PMMA/PEGDMA) in entries 1, 2, and 3 in Table 3 corresponds to DP of PMMA in entries 8 (1.6 h), 9 (3.5 h), and 10 (5.2 h) in Table 2, respectively.
$^c$The DLS peak top value.
$^d$S = sphere, W = worm, and V = vesicle.

Example 4. Synthesis and Characterisation of PMPC$_x$-PLMA$_y$ Block Copolymer by NTMC-CRP and PISA (via NTMC-CRP)

The synthesis of PMPC$_x$-PLMA$_y$ block copolymer with various x and y values was carried out following the method described in Example 1.

Figure 7:
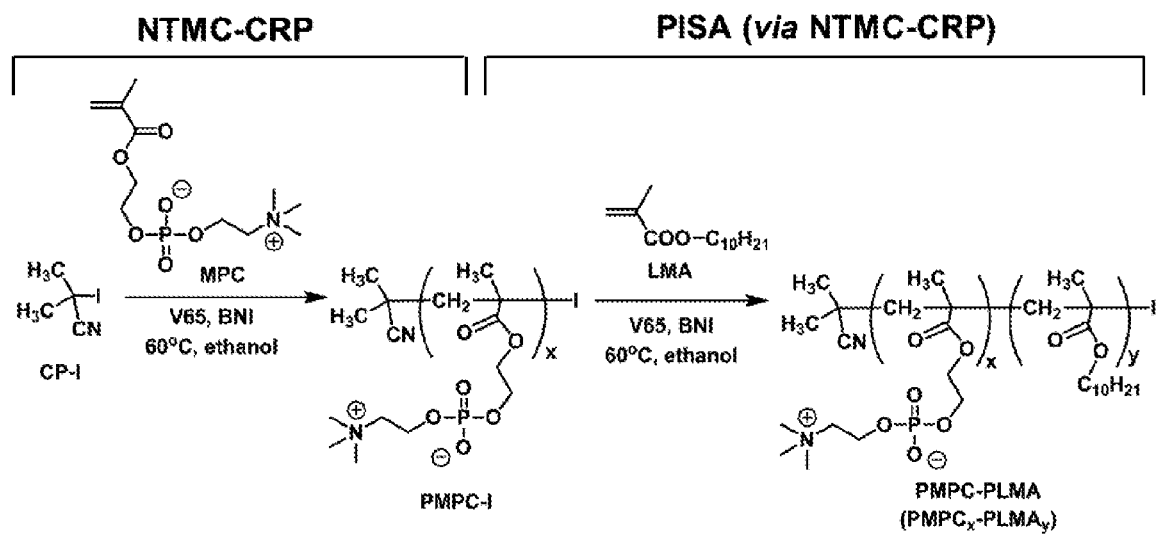
FIG. 7 Depicts the synthesis of PMPC$_x$-PLMA$_y$ (an embodiment of current invention) by NTMC-CRP and PISA (via NTMC-CRP).

PMPC-I macroinitiator with a DP of 24 was first synthesised using MPC monomers, CP-I (as initiating dormant species), V65 (azo initiator) and tetrabutylammonium iodide (BNI, as catalyst) in ethanol (60 wt %) at 60° C. (FIG. 7 and Table 4). The as-synthesised PMPC-I was purified by reprecipitation in a mixture of diethyl ether/methanol (4:1, v/v).

TABLE 4

Synthesis of PMPC-I macroinitiators.

| Entry | [MPC]$_0$/[CP-I]$_0$/ [V65]$_0$/[BNI]$_0$ (mM) | T (° C.) | t (h) | Conv. (%) | M$_n$ | PDI |
|---|---|---|---|---|---|---|
| 1 | 8000/160/80/80 | 60 | 2.5 | 20 | 7000 (DP = 24) | 1.11 |

The synthesis of PMPC$_x$-PLMA$_y$ block copolymer was then carried out using the as-synthesised PMPC-I (as the macroinitiators), CP-I, V65 and BNI in ethanol (90 wt %) at 60° C. via the PISA process (FIG. 7 and Table 5a).

The DP of PMPC-I was calculated by the molecular weight obtained from GPC, using water as eluent. As the block polymers were not soluble in water, GPC was not performed and the DP of the block polymers was calculated using proton NMR.

TABLE 5a

Synthesis of PMPC$_x$-PLMA$_y$ block copolymer

Figure 8:
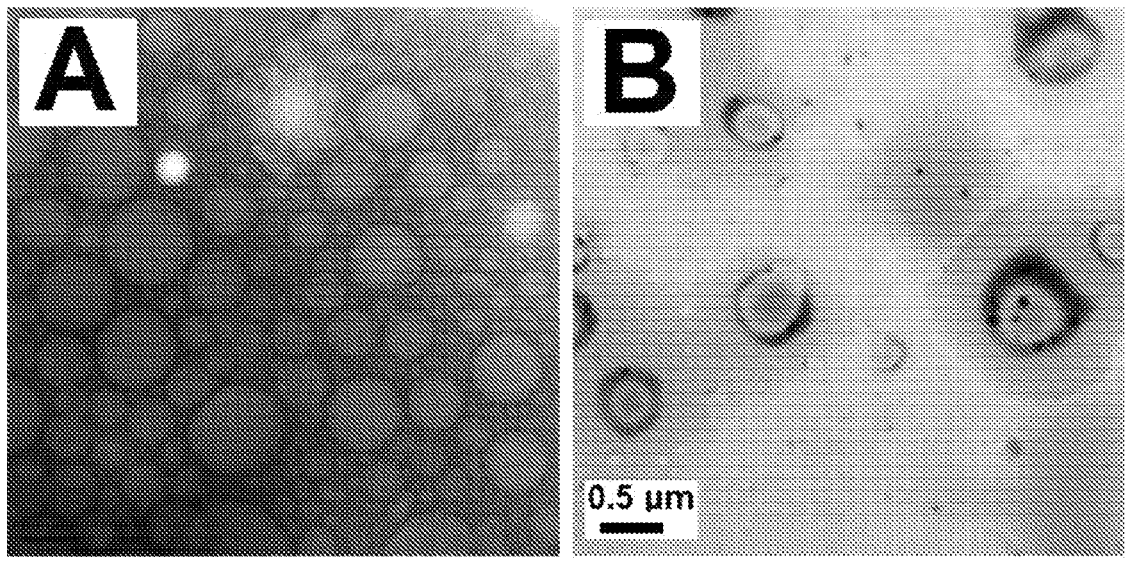
FIG. 8 Depicts the TEM images of PMPC$_x$-PLMA$_y$ self-assemblies: (A) PMPC$_{24}$-PLMA$_y$ generated in PISA for 3 h (y is not determined); and (B) PMPC$_{24}$-PLMA$_{480}$.

| [MPC]$_0$/[CP-I]$_0$/ [V65]$_0$/[BNI]$_0$ (mM) | T (° C.) | t (h) | Conv. (%) | M$_n$ | PDI | Size (nm) | Structure | Code in FIG. 8 |
|---|---|---|---|---|---|---|---|---|
| 8000/160/80/80 | 60 | 3 | 20 | — | — | 150 | sphere + vesicle | A |
| | | 18 | 88 | 128000 (DP = 24 + 480) | — | 350 | vesicle | B |

Example 5. Synthesis and Characterisation of PMMA$_y$-PMAA-PMMA$_y$ Block Copolymer by NTMC-CRP and PISA The synthesis of the block copolymer was extended to using a bi-functional initiator to give the PMMA$_y$-PMAA$_x$-PMMA$_y$ block copolymer, following the method described in Example 1.

Figure 9:
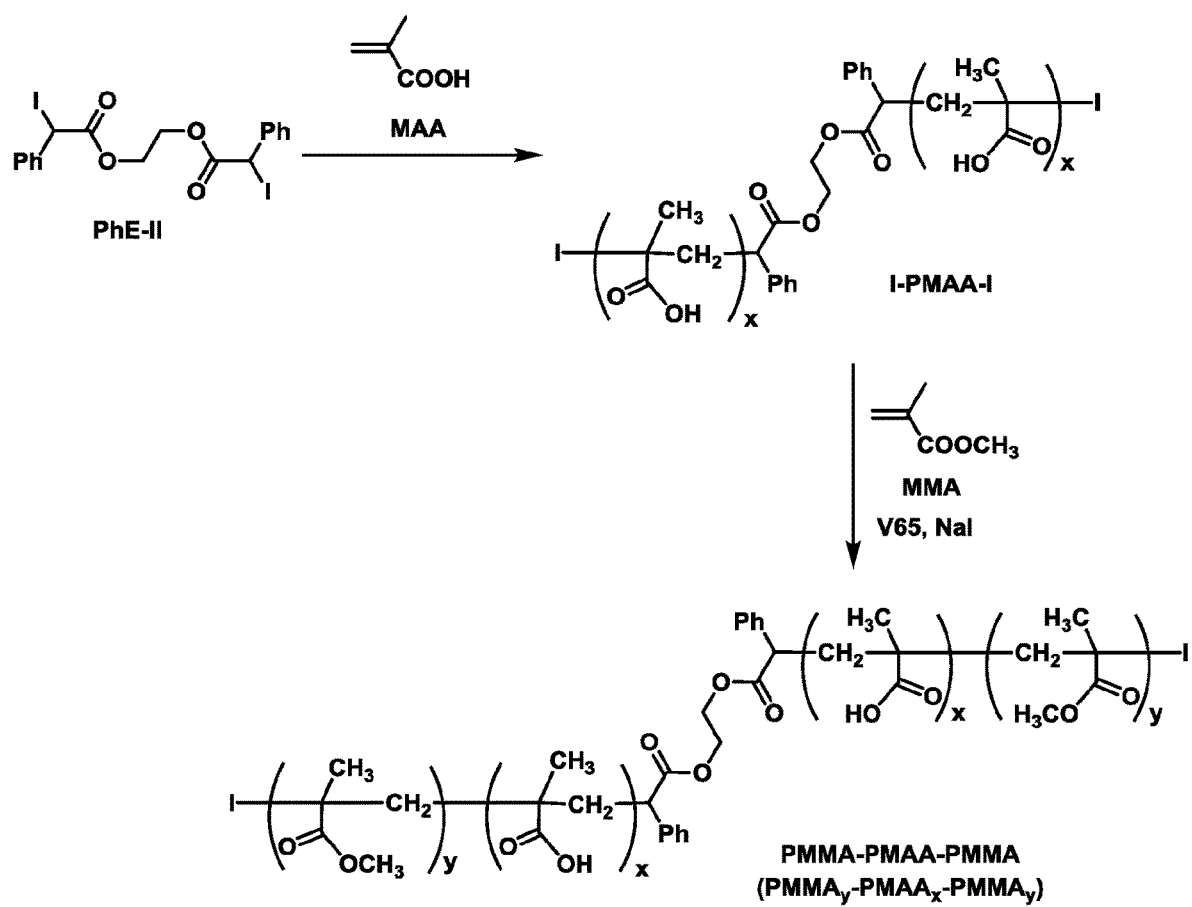
FIG. 9 Depicts the synthesis of PMMA$_y$-PMAA-PMMA$_y$ (an embodiment of current invention) by NTMC-CRP and PISA (via NTMC-CRP).
Figure 10:
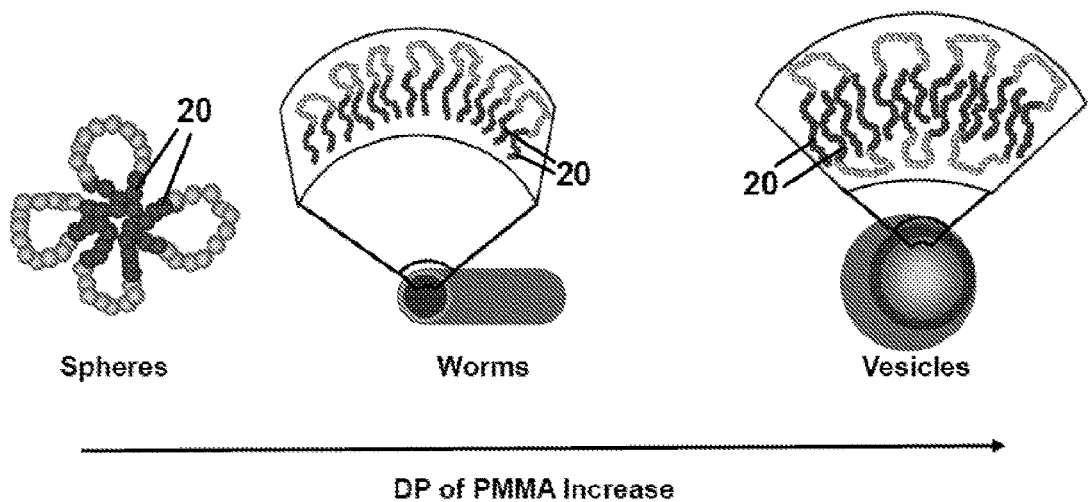
FIG. 10 Depicts the effect of increasing the DP of PMMA segments (20) of PMMA$_y$-PMAA$_x$-PMMA$_y$ on the structures of the self-assemblies.
Figure 11:
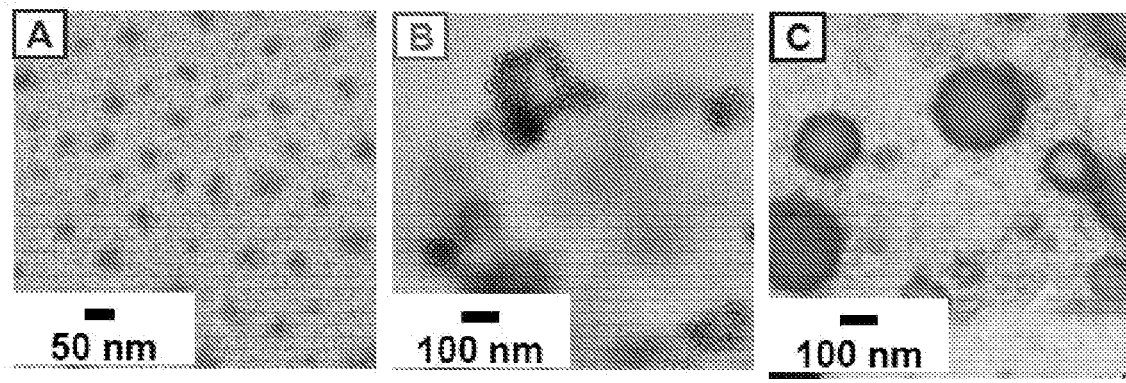
FIG. 11 Depicts the TEM images of: (A) PMMA$_{82}$-PMAA$_{30}$-PMMA$_{82}$; (B) PMMA$_{134}$-PMAA$_{30}$-PMMA$_{134}$; and (C) PMMA$_{170}$-PMAA$_{30}$-PMMA$_{170}$.

I-PMAA-1 macroinitiator with a DP of 30 was first synthesised using MAA monomers, PhE-II (as initiating dormant species), NaI as a catalyst, water as a solvent (50 wt %), at 45° C. for 1.3 h (FIG. 9). The as-synthesised I-PMAA-1 was purified by reprecipitation in a diethyl ether.

It was observed that the DP of the PMMA block can lead to the formation of self-assemblies with different morphologies. As the DP of the PMMA segments (20) increased, the morphology of the self-assemblies changed from spheres to worms to vesicles, as shown in FIGS. 10 and 11A-C—summarised in Table 5b.

The presence of two chain ends with similar solubility property can allow self-assembling to occur such that no chain ends of the block copolymer chain are outside the periphery of the structures. This produces polymeric structures with low viscosity and high lubrication, with better penetration through the phospholipid bilayers of cells.

TABLE 5b

Synthesis of $PMMA_y$-$PMAA_x$-$PMMA_y$ block copolymer

| DP of I-PMAA-I | $[MMA]_0$/[I-PMAA-I]$_0$/ $[V65]_0$/[NaI]$_0$ (mM) | t (h) | Conv. (%) | $M_n$ | PDI | Size (nm) | Structure | Code in FIG. 11 |
|---|---|---|---|---|---|---|---|---|
| 30 | 8000/20/10/40 | 2.5 | 22 | 6700 (DP = 30 + 37) | 1.18 | — | Soluble | — |
| | | 4 | 25 | 11200 (DP = 30 + 82) | 1.20 | 50 | Spheres | A |
| | | 5.5 | 33 | 16000 (DP = 30 + 134) | 1.21 | 120 | Worms | B |
| | | 7.5 | 57 | 18900 (DP = 30 + 163) | 1.21 | 179 | Vesicles | — |
| | | 9 | 64 | 20000 (DP = 30 + 170) | 1.24 | 250 | Vesicles | C |
| | | 20 | 80 | 24000 (DP = 30 + 210) | 1.24 | 300 | Vesicles | — |

Figure 12:
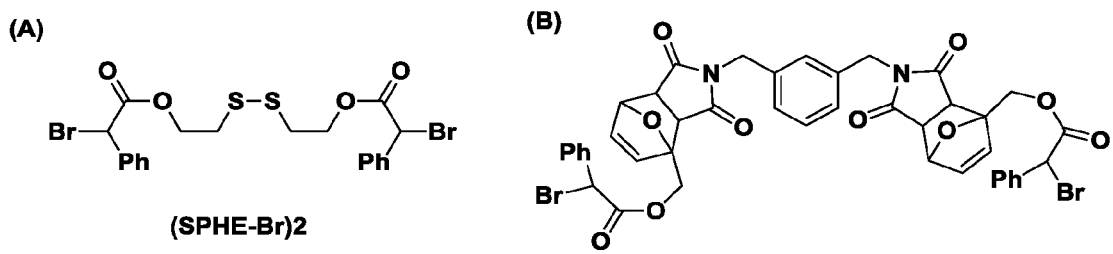
FIG. 12 Depicts the molecular structures of: (A) redox-responsive initiator; and (B) thermos-responsive initiator.

Example 6. Synthesis and Characterisation of Block Copolymer Synthesised Using Stimuli-Responsive Initiators The currently claimed invention can be extended to the use of stimuli-responsive initiators to produce responsive block copolymer or assemblies. Such stimuli-responsive polymeric assemblies can respond to external stimuli like reducing agents (e.g. $NaBH_4$) or heat to result in structural changes in the morphologies (i.e. by cleavage of S—S bond or structural changes), which can potentially be use in releasing and delivery of materials encapsulated within the polymeric assemblies. Some examples of stimuli-responsive initiators are the redox-responsive initiator and thermos-responsive initiators as shown in FIGS. 12A and B, respectively.

Figure 13:
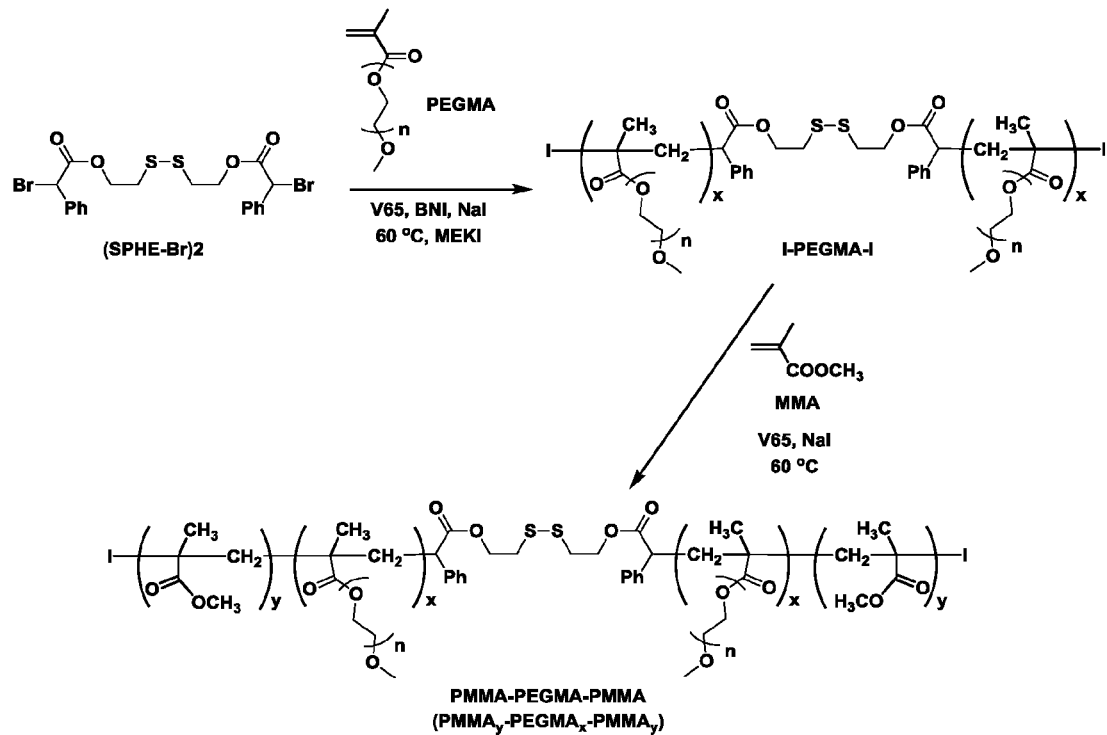
FIG. 13 Depicts the synthesis of redox-responsive PMMA$_y$-PEGMA$_x$-PMMA$_y$ with (SPHEBr)2 as the initiator.

In this example, the redox-responsive initiator (SPHE-Br)2 was used to synthesise the redox-responsive block copolymer (FIG. 13 and Table 6).

Figure 14:
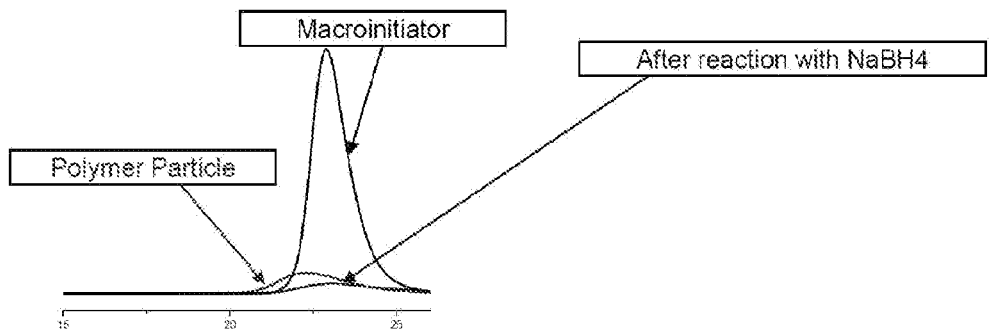
FIG. 14 Depicts the GPC chromatographs of PPEGMA-I macroinitiator, PPEGMA-PMMA-PPEGMA block copolymer (polymer particle), and PPEGMA-PMMA-PPEGMA block copolymer after reaction with sodium borohydride (NaBH$_4$), as discussed in example 6.

The I-PEGMA-1 macroinitiator was synthesised using PEGMA as a monomer, (SPHE-Br)2 as an initiator, BNI as a catalyst and NaI for in situ halogen exchange and methyl ethyl ketone (MEK) as a solvent at 60° C. for 3.5 h (Table 7). The as-synthesised I-PPEGMA-1 was purified by reprecipitation from a mixture of hexane and diethyl ether (1:1, v/v) as a non-solvent. The obtained macroinitiator was used in PISA to generate self-assemblies and the obtained block copolymer was cleaved using $NaBH_4$. The cleaving of S—S bond was indicated by the GPC chromatographs as shown in FIG. 14.

TABLE 6

Synthesis of I-PEGMA-I macroinitiators using the redox-responsive initiator (SPHE-Br)2

| $[PEGMA]_0$/[Initiator]$_0$/ $[V65]_0$/[BNI]$_0$/[NaI]$_0$ (mM) | T (° C.) | t (h) | Conv. (%) | $M_n$ | PDI |
|---|---|---|---|---|---|
| 8000/40/80/80/90 in MEK (60 wt %) | 60 | 3.5 | 75 | 15000 (DP = 50) | 1.31 |

TABLE 7

Synthesis of redox-responsive PMMA-PEGMA-PMMA with (SPHE-Br)2 as the initiator

| $[MMA]_0$/[I-EGMA-]$_0$/ $[V65]_0$/[NaI]$_0$/ (mM) | T (° C.) | t (h) | Conv. (%) | $M_n$ | PDI$^a$ | Size (nm) | PDI$^b$ | Structure |
|---|---|---|---|---|---|---|---|---|
| 8000/20/20/160 | 60 | 16 | 60 | 22000 (DP = 50 + 70) | 1.45 | 200 | 0.212 | — |

$^a$Obtained from GPC (molecular weight distribution)
$^b$Obtained from DLS (assembly size distribution)

Example 7. Synthesis and Characterisation of PPEGMA$_x$-PMMA$_y$ Block Copolymer by NTMC-CRP and PISA (Via NTMC-CRP, in Water or Ethanol)

Synthesis of PPEGMA-1 Macroinitiators

PPEGMA-1 macroinitiators were prepared using tetrabutylammonium iodide (BNI) as a catalyst. An in situ generated alkyl iodide (R—I) was utilised as an initiator instead of an isolated R—I. Typically, iodine (I$_2$) and an azo compound, i.e., 2,2-azobis(2,4-dimethylvaleronitrile) (an azo initiator, V65)) were used to generate an R—I in situ. V65 generated the alkyl radical (R') which reacted with I$_2$ to form R—I.

In a typical reaction, a mixture of poly(ethylene glycol) methyl ether methacrylate (PEGMA) (average molecular weight=300, 8 M, monomer), I$_2$ (40 mM), V65 (160 mM), BNI (80 mM, catalyst), and ethanol (20 wt %, solvent) was heated at 60° C. for 3.5 h (Table 8, entry 1). At 3.5 h, the monomer conversion reached 75%. The as-synthesised polymer was purified by reprecipitation using a mixture of hexane and diethyl ether (1:1, v/v) as a non-solvent to give macroinitiators with DPs 90, 52, 46, 33, and 27 (Table 8).

TABLE 8

Synthesis of PPEGMA-I macroinitiators using PEGMA, I$_2$, V65, and BNI in 20 wt % ethanol.

| Entry | [PEGMA]$_0$/[I$_2$]$_0$/[V65]$_0$/[BNI]$_0$ (mM)$^a$ | T (° C.) | t (h) | Conv.$^b$ (%) | M$_n$$^c$ | DP$^c$ | Đ$^c$ |
|---|---|---|---|---|---|---|---|
| 1 | 8000/40/160/80 | 60 | 3.5 | 75 | 27000 | 90 | 1.31 |
| 2 | 8000/80/320/80 | 60 | 3.5 | 73 | 13800 | 46 | 1.21 |
|   |                |    | 3.6 | —  | 15600 | 52 | 1.24 |
| 3 | 8000/160/640/80 | 60 | 4  | 70 | 9900  | 33 | 1.16 |
|   |                |    | 3.7 | —  | 8100  | 27 | 1.16 |

$^a$Solution polymerisation in 20 wt % ethanol (solvent).
$^b$Monomer conversions were calculated from $^1$H NMR analyses.
$^c$The M$_n$, DP, and Đ values of PPEGMA-I were PMMA-calibrated GPC values after purification (reprecipitation).

PISA in Water

Typically, a mixture of MMA (8 M, monomer), PPEGMA$_{90}$-I (20 mM, macroinitiator), 4,4-azobis(4-cyanovaleric acid) (V501) (40 mM, azo initiator), NaI (160 mM, catalyst), and water (90 wt %, solvent) was heated at 60° C. (Table 9, entry 3). The pH of the solution was adjusted to 7 by adding sodium bicarbonate (NaHCO$_3$). Different PPEGMA$_{90}$-PMMA$_y$ block copolymers at different polymerisation times (up to 4 h) were obtained (with monomer conversion=83%, where y is the DP of PMMA). At each sampling time, a small portion of the reaction mixture was taken out from the reactor vessel, divided in three parts. The first part was dried and subjected to GPC analysis. The second part was diluted with DMSO-d$_6$ and analysed by $^1$H NMR. The third part was diluted by 50 times with water and was used as the stock solution for the subsequent dynamic light scattering (DLS) and transmission electron microscope (TEM) studies. The reaction was repeated using PPEGMA-1 macroinitiators with DP of 33 and 46, with different conditions as summarised in Table 9. The as-synthesised polymers were characterised by TEM as shown in FIGS. 17 and 18.

PISA in Ethanol

Figure 15:
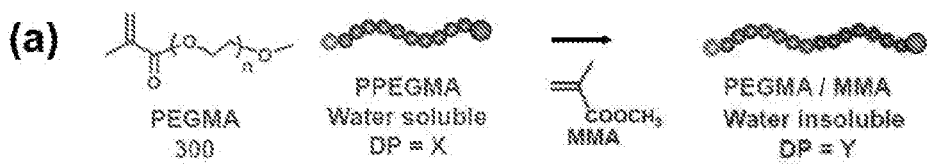
FIG. 15 Depicts: (a) the synthesis of PPEGMA$_x$-PMMA$_y$ block copolymers; and (b) phase diagram of the self-assemblies generated in the ethanolic dispersion PISA process of PPEGMA$_x$-PMMA$_y$.
Figure 15:
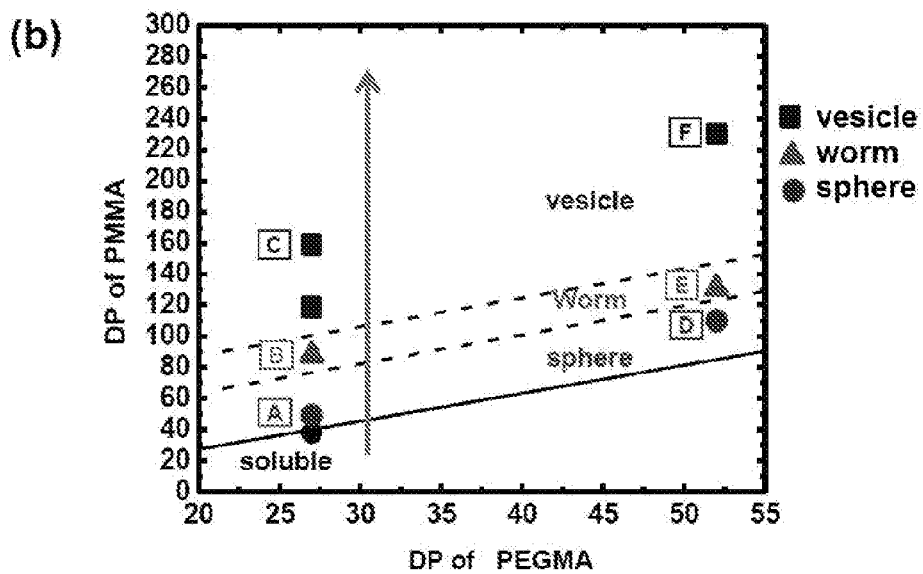
Figure 16:
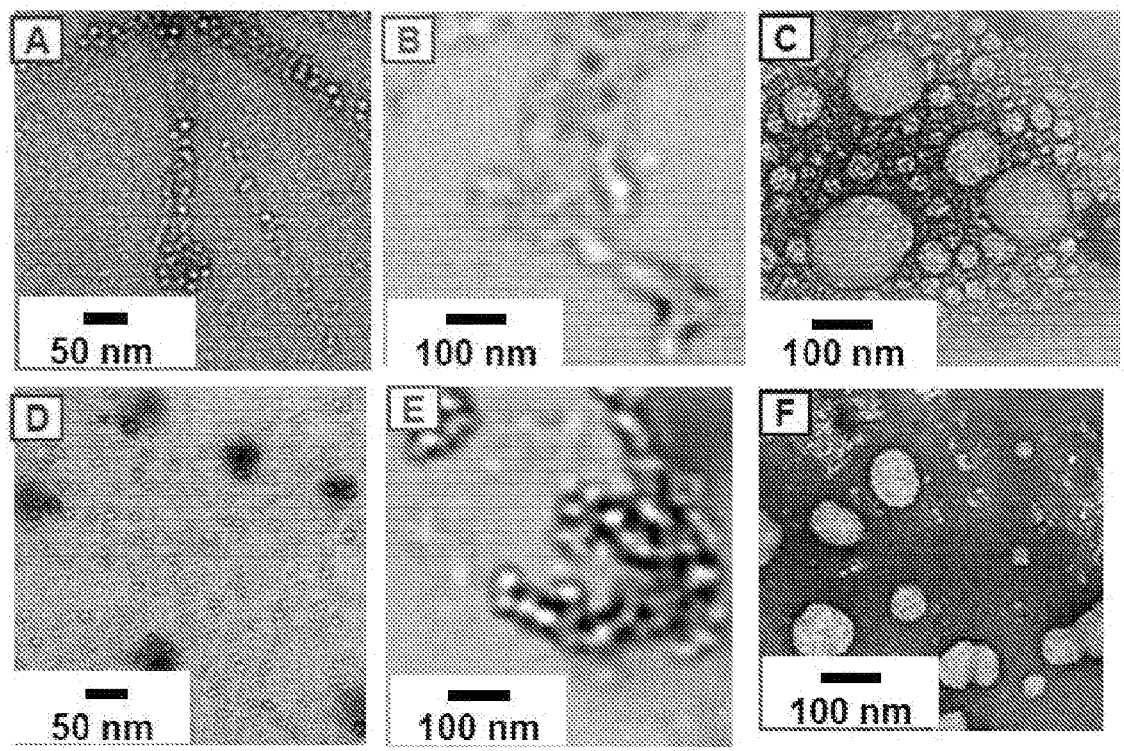
FIG. 16 Depicts the TEM images of the self-assemblies obtained in the ethanolic dispersion PISA process: (A) PPEGMA$_{27}$-PMMA$_{49}$; (B) PPEGMA$_{27}$-PMMA$_{88}$; (C) PPEGMA$_{27}$-PMMA$_{159}$; (D) PPEGMA$_{52}$-PMMA$_{110}$; (E) PPEGMA$_{52}$-PMMA$_{131}$; and (F) PPEGMA$_{52}$-PMMA$_{230}$.

Typically, a mixture of MMA (8 M, monomer), PPEGMA$_{27}$-I (20 mM, macroinitiator), V65 (20 mM, azo initiator), NaI (160 mM, catalyst), and ethanol (90 wt %, solvent) was heated at 60° C. (Table 10, entry 1). Different PPEGMA$_{27}$-PMMA$_y$ block copolymers were obtained at different polymerisation times. The reaction was also repeated using PPEGMA-1 with DP of 52 with different conditions as summarised in Table 10. The as-synthesised block polymers were characterised by TEM (FIGS. 15b and 16).

TABLE 9

Synthesis of PPEGMA$_x$-PMMA$_y$ via PISA in water, using MMA, PPEGMA-I, V501, and NaI in 90 wt % water at 60° C.

| Entry | DP of PPEGMA | [MMA]$_0$/[PPEGMA-I]$_0$/[NaI]$_0$/[V501]$_0$ (mM)$^a$ | t (h) | Conv (%) | DP of PMMA$^b$ | Đ$^b$ | Symbol of Block Copolymer | f$_{PMMA}$ | Hydrodynamic Diameter$^c$ in DLS (nm) | Size Distribution Index in DLS | Assembly Structure$^d$ | Code in FIGS. 17 and 18 |
|---|---|---|---|---|---|---|---|---|---|---|---|---|
| 1 | 33 | 8000/20/160/40 | 1.2 | 35 | 21 | 1.17 | PPEGMA$_{33}$-PMMA$_{21}$ | 0.18 | 30 | 0.124 | S | |
|   |    |                | 1.8 | 43 | 31 | 1.21 | PPEGMA$_{33}$-PMMA$_{31}$ | 0.24 | 39 | 0.134 | S | A |
|   |    |                | 2.3 | 50 | 49 | 1.21 | PPEGMA$_{33}$-PMMA$_{49}$ | 0.33 | 60 | 0.284 | S | |
|   |    |                | 2.8 | 57 | 61 | 1.21 | PPEGMA$_{33}$-PMMA$_{61}$ | 0.38 | 110 | 0.352 | S + V | B |
|   |    |                | 3.8 | 67 | 91 | 1.24 | PPEGMA$_{33}$-PMMA$_{91}$ | 0.48 | 158 | 0.366 | V | C |
| 2 | 46 | 8000/20/160/40 | 1   | 20 | 16 | 1.31 | PPEGMA$_{46}$-PMMA$_{16}$ | 0.13 | 60 | 0.113 | S | |
|   |    |                | 1.5 | 30 | 26 | 1.32 | PPEGMA$_{46}$-PMMA$_{26}$ | 0.16 | 75 | 0.137 | S | D |
|   |    |                | 2   | 35 | 34 | 1.31 | PPEGMA$_{46}$-PMMA$_{34}$ | 0.20 | 85 | 0.143 | S | |
|   |    |                | 2.5 | 41 | 42 | 1.32 | PPEGMA$_{46}$-PMMA$_{42}$ | 0.23 | 93 | 0.127 | S | |
|   |    |                | 3   | 54 | 58 | 1.28 | PPEGMA$_{46}$-PMMA$_{58}$ | 0.30 | 100 | 0.210 | S | |
|   |    |                | 3.5 | 66 | 78 | 1.26 | PPEGMA$_{46}$-PMMA$_{78}$ | 0.36 | 135 | 0.329 | S + V | E |
|   |    |                | 5   | 75 | 140 | 1.35 | PPEGMA$_{46}$-PMMA$_{140}$ | 0.50 | 165 | 0.284 | V | F |
| 3 | 90 | 8000/20/160/40 | 1.2 | 20 | 15 | 1.27 | PPEGMA$_{90}$-PMMA$_{15}$ | 0.05 | 35 | 0.243 | S | |
|   |    |                | 1.8 | 28 | 25 | 1.27 | PPEGMA$_{90}$-PMMA$_{25}$ | 0.08 | 45 | 0.203 | S | G |
|   |    |                | 2.3 | 35 | 35 | 1.27 | PPEGMA$_{90}$-PMMA$_{35}$ | 0.12 | 65 | 0.196 | S | |

TABLE 9-continued

Synthesis of PPEGMA$_x$-PMMA$_y$ via PISA in water, using MMA, PPEGMA-I, V501, and NaI in 90 wt % water at 60° C.

| Entry | DP of PPEGMA | [MMA]$_0$/ [PPEGMA-I]$_0$/ [NaI]$_0$/[V501]$_0$ (mM)$^a$ | t (h) | Conv (%) | DP of PMMA$^b$ | Đ$^b$ | Symbol of Block Copolymer | f$_{PMMA}$ | Hydro-dynamic Diameter$^c$ in DLS (nm) | Size Distribution Index in DLS | Assembly Structure$^d$ | Code in FIGS. 17 and 18 |
|---|---|---|---|---|---|---|---|---|---|---|---|---|
|  |  |  | 2.8 | 60 | 110 | 1.42 | PPEGMA$_{90}$-PMMA$_{110}$ | 0.30 | 100 | 0.139 | S + V | H |
|  |  |  | 4 | 83 | 480 | 1.50 | PPEGMA$_{90}$-PMMA$_{480}$ | 0.64 | 370 | 0.590 | V | I |

$^a$The mixture of PPEGMA-I, NaI, and V501 was diluted with water (water content = 90 wt %) and mixed with MMA at the described concentration.
$^b$DP and Đ were recorded using DMF-GPC after drying.
$^c$The size was the DLS peak-top value.
$^d$S = sphere and V = vesicle.

TABLE 10

Synthesis of PPEGMA$_x$-PMMA$_y$ via PISA in ethanol, using MMA, PPEGMA-I, V65, and NaI in 90 wt % ethanol at 60° C.

| Entry | DP of PPEGMA | [MMA]$_0$/ [PPEGMA-I]$_0$/ [NaI]$_0$/[V65]$_0$ (mM)$^a$ | t (h) | Conv (%) | DP of PMMA$^b$ | Đ$^b$ | Symbol of Block Copolymer | f$_{PMMA}$ | Hydrodynamic Diameter$^c$ in DLS (nm) | Assembly Structure$^d$ | Code in FIGS. 15b and 16 |
|---|---|---|---|---|---|---|---|---|---|---|---|
| 1 | 27 | 8000/20/20/80 | 1.7 | 32 | 38 | 1.17 | PPEGMA$_{27}$-PMMA$_{38}$ | 0.31 | — | Soluble |  |
|  |  |  | 2.5 | 38 | 49 | 1.21 | PPEGMA$_{27}$-PMMA$_{49}$ | 0.38 | 35 | S | A |
|  |  |  | 4 | 46 | 88 | 1.21 | PPEGMA$_{27}$-PMMA$_{88}$ | 0.52 | 91 | W | B |
|  |  |  | 7 | 52 | 119 | 1.21 | PPEGMA$_{27}$-PMMA$_{119}$ | 0.60 | 154 | V |  |
|  |  |  | 17 | 72 | 159 | 1.24 | PPEGMA$_{27}$-PMMA$_{159}$ | 0.66 | 201 | V | C |
| 2 | 52 | 8000/20/20/80 | 2.5 | 42 | 110 | 1.21 | PPEGMA$_{52}$-PMMA$_{110}$ | 0.41 | 30 | S | D |
|  |  |  | 5 | 55 | 131 | 1.21 | PPEGMA$_{52}$-PMMA$_{131}$ | 0.46 | 80 | W | E |
|  |  |  | 15 | 70 | 230 | 1.23 | PPEGMA$_{52}$-PMMA$_{230}$ | 0.61 | 215 | V | F |

$^a$The mixture of PPEGMA-I, NaI, and V65 was diluted with ethanol (ethanol content = 90 wt %) and mixed with MMA at the described concentration.
$^b$DP and Đ were recorded using DMF-GPC after drying.
$^c$The size was the DLS peak-top value.
$^d$S = sphere, W = worm, and V = vesicle.

The invention claimed is:

1. A nanoparticulate composition comprising:
nanoparticles formed from an amphipathic block copolymer comprising a hydrophilic block and a hydrophobic block, where the nanoparticles are provided in the form of micelles, cylindrical worm structures or vesicles and the size of the nanoparticles is from 25 to 500 nm, wherein:
the composition is substantially free of compounds comprising sulfur;
the composition is substantially free of a heavy metal; and
the composition includes an active agent encapsulated in the nanoparticles.

2. The composition according to claim 1, wherein the amphipathic block copolymers are terminated by a halogen atom.

3. The composition according to claim 1, wherein the active agent is selected from one or more of the group consisting of vitamin C, peptides, glycerol, dyes, flavours, perfume oils, citronellal, silicon oils, organosilicons, pesticides, Beta-carotene and a pharmacologically active agent.

4. The composition according to claim 1, wherein when the nanoparticles are in the form of a vesicle, the amphipathic block copolymer is arranged in the form of a membrane with an outer and inner surface, which inner surface defines a core region.

5. The composition according to claim 4, wherein the core region comprises one or both of an active agent and a liquid.

6. The composition according to claim 4, wherein the amphipathic block copolymer is arranged so that the outer and inner surface of the membrane are formed from the hydrophilic blocks of the copolymer.

7. The composition according to claim 6, wherein one or more of the following apply:
(AA) the composition further comprises a hydrophilic active agent that is substantially encapsulated in the core region of the vesicle;
(BB) the composition further comprises a hydrophobic active agent that is substantially encapsulated in the membrane of the vesicle; or
(CC) the composition further comprises a polar liquid that is encapsulated in the core region of the vesicle.

8. The composition according to claim 4, wherein the amphipathic block copolymer is arranged so that the outer and inner surface of the membrane are formed from the hydrophobic blocks of the copolymer.

9. The composition according to claim 8, wherein one or more of the following apply:
(DD) the composition further comprises a hydrophobic active agent that is substantially encapsulated in the core region of the vesicle;
(EE) the composition further comprises a hydrophilic active agent that is substantially encapsulated in the membrane of the vesicle; or
(FF) the composition further comprises a non-polar liquid that is encapsulated in the core region of the vesicle.

10. The composition according to claim 1, wherein one of the following applies:
(A) when the nanoparticles are in the form of a micelle, the amphipathic block copolymer has an average ratio of hydrophobic repeating units to hydrophilic repeating units of from 1:100 to 10:1 or vice versa; or (B) when the nanoparticles are in the form of cylindrical worm structures, the amphipathic block copolymer has an average ratio of hydrophobic repeating units to hydrophilic repeating units of from 1:1 to 100:1 or vice versa.

11. The composition according to claim 1, wherein the amphipathic block copolymer is a poly(acrylic acid-co-acrylate ester) or a poly((polyethylene glycol ether methacrylate)-co-acrylate ester.

12. The composition according to claim 1, wherein the amphipathic block copolymer is crosslinked.

13. A method of forming a nanoparticulate composition according to claim 1 using polymerisation induced self-assembly, the method comprising the step of forming a block copolymer by reacting a monomeric material with a macroinitiator compound in the presence of an initiator compound, a catalyst and a solvent, wherein:
   if the monomeric material polymerises to provide a hydrophobic polymer block, then the macroinitiator compound is a hydrophilic polymer or oligomer or if the monomeric material polymerises to provide a hydrophilic polymer block, then the macroinitiator compound is a hydrophobic polymer or oligomer;
   the macroinitiator compound is terminated with a halogen atom;
   the monomeric material, the macroinitiator compound, the initiator compound, the catalyst and the solvent are all substantially free of compounds comprising sulfur; and
   the monomeric material, the macroinitiator compound, the initiator compound, the catalyst and the solvent are all substantially free of a heavy metal.

14. The method according to claim 13, wherein:
   (i) the monomeric material is an acrylate ester, and the macroinitiator compound is a poly(acrylic acid) or an oligo(acrylic acid); or
   (ii) the monomeric material is an acrylic acid and the macroinitiator compound is a poly(acrylate ester) or an oligo(acrylate ester).

15. The method according to claim 13, wherein the step of forming a block copolymer is conducted in the presence of a crosslinking agent.

16. The method according to claim 13, wherein the step of forming a block copolymer is conducted in the presence of an active agent.

17. The method according to claim 13, wherein after the nanoparticle has been formed an active agent is encapsulated into the nanoparticle by osmosis.

18. The method according to claim 13, wherein one of the following applies:
   (a) the nanoparticles are obtained as vesicles when the molar ratio of monomeric material to macroinitiator compound in the solvent is from 100:1 to 500:1, and the reaction is allowed to occur for a period of time such that an average ratio of monomeric material repeating units to macroinitiator repeating units from 1:9 to at least 9:1 is obtained;
   (b) the nanoparticles are obtained as micelles when the molar ratio of monomeric material to macroinitiator compound in the solvent is from 40:1 to 100:1 and the reaction is allowed to occur for a period of time such that an average ratio of monomeric material repeating units to macroinitiator repeating units from 1:100 to 10:1 is obtained; or
   (c) the nanoparticles are obtained as cylindrical worm structures when the molar ratio of monomeric material to macroinitiator compound in the solvent is from 40:1 to 200:1 and the reaction is allowed to occur for a period of time such that an average ratio of monomeric material repeating units to macroinitiator repeating units from 1:1 to 100:1 is obtained.

19. The method according to claim 13, wherein the macroinitiator compound is formed by polymerising a monomeric material with a dormant initiator compound in the presence of an initiator compound, a catalyst and a solvent, wherein
   the dormant initiator compound is a hydrocarbon comprising a halogen atom;
   the monomeric material, the dormant initiator compound, the initiator compound, the catalyst and the solvent are all substantially free of compounds comprising sulfur; and
   the monomeric material, the dormant initiator compound, the initiator compound, the catalyst and the solvent are all substantially free of a heavy metal.

* * * * *